United States Patent
Katagiri et al.

(10) Patent No.: US 10,370,325 B2
(45) Date of Patent: Aug. 6, 2019

(54) CYANATE ESTER COMPOUND, CURABLE RESIN COMPOSITION CONTAINING THE COMPOUND, AND HARDENED PRODUCT THEREOF

(71) Applicant: MITSUBISHI GAS CHEMICAL COMPANY, INC., Tokyo (JP)

(72) Inventors: Masayuki Katagiri, Niigata (JP); Tatsuya Shima, Niigata (JP); Keita Tokuzumi, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/560,708

(22) PCT Filed: Feb. 19, 2016

(86) PCT No.: PCT/JP2016/054850
§ 371 (c)(1),
(2) Date: Sep. 22, 2017

(87) PCT Pub. No.: WO2016/158066
PCT Pub. Date: Oct. 6, 2016

(65) Prior Publication Data
US 2018/0105488 A1   Apr. 19, 2018

(30) Foreign Application Priority Data
Mar. 31, 2015   (JP) .................................. 2015-072689

(51) Int. Cl.
C07C 261/02   (2006.01)
C08G 14/12   (2006.01)
(Continued)

(52) U.S. Cl.
CPC ............ *C07C 261/02* (2013.01); *C08G 14/12* (2013.01); *C08G 59/20* (2013.01); *C08G 61/02* (2013.01);
(Continued)

(58) Field of Classification Search
CPC ...... C07C 261/02; C08G 61/02; C08G 73/06; C08G 14/12; C08J 5/04; C08J 5/24;
(Continued)

(56) References Cited

U.S. PATENT DOCUMENTS 4,709,008 A   11/1987 Shimp
6,342,577 B1 * 1/2002 Konarski ........... C08G 59/4014
                                                    257/E21.503
(Continued)

FOREIGN PATENT DOCUMENTS

CN   1237186 A   12/1999
JP   60-31585   2/1985
(Continued)

OTHER PUBLICATIONS

Yan, H-Q, et al., Synthe, cure kinetics and thermal properties of the 2,7-dihydroxynaphthalene dicyanate, 2003, Polymer vol. 44, issue 26, pp. 7861-7867 (Year: 2003).*
(Continued)

*Primary Examiner* — Yate' K Cutliff
(74) *Attorney, Agent, or Firm* — Greenblum & Bernstein, P.L.C.

(57) ABSTRACT

The present invention provides a novel cyanate ester compound which has excellent solvent solubility and from which a hardened product having a low coefficient of thermal expansion and excellent flame retardancy and heat resistance is obtained. The present invention is a cyanate ester compound obtained by cyanating a naphthol-dihydroxynaphthalene aralkyl resin or a dihydroxynaphthalene aralkyl resin.

20 Claims, 5 Drawing Sheets

| Retention time | Area % |
|---|---|
| 17.9 min. | 17.9% |
| 18.2 min. | 10.6% |
| 18.6 min. | 15.3% |
| 19.1 min. | 22.4% |
| 19.7 min. | 29.1% |
| 21.4 min. | 4.8% |

(51) Int. Cl.

| | |
|---|---|
| *C08G 59/20* | (2006.01) |
| *C08G 61/02* | (2006.01) |
| *C08J 5/04* | (2006.01) |
| *C08J 5/24* | (2006.01) |
| *C08G 65/18* | (2006.01) |
| *C09J 161/06* | (2006.01) |
| *C09J 163/00* | (2006.01) |
| *C08L 61/04* | (2006.01) |
| *C08L 61/34* | (2006.01) |
| *C08L 63/00* | (2006.01) |
| *C08L 65/00* | (2006.01) |
| *H01L 23/14* | (2006.01) |
| *H01L 23/29* | (2006.01) |
| *H01L 23/31* | (2006.01) |
| *C09J 11/06* | (2006.01) |
| *C08G 73/06* | (2006.01) |
| *C09J 179/04* | (2006.01) |

(52) U.S. Cl.
CPC ............ *C08G 65/18* (2013.01); *C08J 5/04* (2013.01); *C08J 5/24* (2013.01); *C08L 61/04* (2013.01); *C08L 61/34* (2013.01); *C08L 63/00* (2013.01); *C08L 65/00* (2013.01); *C09J 11/06* (2013.01); *C09J 161/06* (2013.01); *C09J 163/00* (2013.01); *H01L 23/14* (2013.01); *H01L 23/29* (2013.01); *H01L 23/31* (2013.01); *C08G 73/06* (2013.01); *C09J 179/04* (2013.01)

(58) Field of Classification Search
CPC ......... C08L 61/04; C08L 61/34; C08L 63/00; C08L 65/00; C09J 11/06; C09J 161/06; C09J 163/00; H01L 23/14; H01L 23/29; H01L 23/31
See application file for complete search history.

(56) References Cited

U.S. PATENT DOCUMENTS

| | | | |
|---|---|---|---|
| 2009/0130488 A1 | 5/2009 | Sugano et al. | |
| 2013/0281640 A1 | 10/2013 | Tsubuku et al. | |
| 2014/0308530 A1 | 10/2014 | Sugano et al. | |
| 2016/0125971 A1 | 5/2016 | Hasebe et al. | |
| 2016/0125972 A1 | 5/2016 | Arii et al. | |

FOREIGN PATENT DOCUMENTS

| | | |
|---|---|---|
| JP | 05-70549 | 3/1993 |
| JP | 06-145309 | 5/1994 |
| JP | 6-234832 | 8/1994 |
| JP | 2613056 | 2/1997 |
| JP | 2006-193607 A | 7/2006 |
| JP | 2010-180147 | 8/2010 |
| JP | 4654770 | 3/2011 |
| JP | 2012-36114 | 2/2012 |
| JP | 5104312 | 12/2012 |
| JP | 2013-53218 | 3/2013 |
| JP | 2014-185222 | 10/2014 |
| JP | 2015-53341 | 3/2015 |
| WO | 2012/057144 | 5/2012 |
| WO | 2013/021869 | 2/2013 |
| WO | 2014/196501 | 12/2014 |
| WO | 2014/203866 | 12/2014 |

OTHER PUBLICATIONS

Hong-qiang Yan et al., "Interpenetrating polymer networks from the novel bismaleimide and cyanate containing naphthalene: Cure and thermal characteristics", European Polymer Journal, vol. 45; May 7, 2009; pp. 2383-2390.

Tsung-Han Ho, "Synthesis of naphthalene containing aralkyl novolac epoxy resins for electronic application", Macromolecular Materials and Engineering, vol. 283; Jun. 20, 2000; pp. 57-61.

International Search Report issued in Patent Application No. PCT/JP2016/054850, dated Mar. 22, 2016.

International Preliminary Report on Patentability issued in PCT/JP2016/054850, dated Oct. 3, 2017, with English translation.

Hong-Qiang Yan et al., "Synthesis, cure kinetics and thermal properties of the 2, 7-dihydroxynaphthalene dicyanate", vol. 44, No. 26, Dec. 1, 2003, pp. 7861-7867.

* cited by examiner

| Retention time | Area % |
|---|---|
| 17.9 min. | 17.9% |
| 18.2 min. | 10.6% |
| 18.6 min. | 15.3% |
| 19.1 min. | 22.4% |
| 19.7 min. | 29.1% |
| 21.4 min. | 4.8% |

| Retention time | Area % |
|---|---|
| 17.6 min. | 24.0% |
| 17.9 min. | 9.9% |
| 18.2 min. | 13.6% |
| 18.7 min. | 19.9% |
| 19.4 min. | 11.2% |
| 19.6 min. | 15.3% |
| 20.7 min. | 2.1% |
| 21.3 min. | 3.0% |
| 21.8 min. | 1.0% |

Retention time  Area %
17.9 min.  34.9%
18.2 min.  14.1%
18.5 min.  18.0%
18.9 min.  20.0%
19.6 min.  13.0%

| Retention time | Area % |
|---|---|
| 17.7 min. | 47.8% |
| 18.1 min. | 17.9% |
| 18.6 min. | 22.0% |
| 19.3 min. | 5.2% |
| 19.5 min. | 7.0% |

Reteintion time    Area %
18.2 min.         29.5%
18.5 min.         17.0%
19.0 min.         25.2%
19.7 min.         28.3%

Retention time    Area %
17.4 min.         26.1%
17.6 min.         10.7%
17.9 min.         15.2%
18.4 min.         21.8%
19.1 min.         24.6%
19.7 min.         1.7%

US 10,370,325 B2

CYANATE ESTER COMPOUND, CURABLE RESIN COMPOSITION CONTAINING THE COMPOUND, AND HARDENED PRODUCT THEREOF

TECHNICAL FIELD

The present invention relates to a cyanate ester compound, a curable resin composition comprising the compound, and a hardened product thereof.

BACKGROUND ART

Cyanate ester compounds are compounds that form triazine rings by curing. Cyanate ester compounds are widely used as starting materials for various functional polymer materials such as composite materials for structures, adhesives, electrical insulating materials, and electric and electronic components, because of their high heat resistance and excellent electrical properties. In recent years, however, there are increasingly strict requirements concerning properties of functional polymer materials as a higher level of performance is required in these fields of application. Examples of such various properties include flame retardancy, heat resistance, low coeffiencies of thermal expansion, low water-absorbing property, low dielectric constant, low dielectric loss tangent, weather resistance, chemical resistance, and high fracture toughness. However, requirements concerning these properties have not always been satisfied so far.

For example, in the field of semiconductor packaging materials, undesired warpage occurs due to the mismatched coefficiency of thermal expansion between semiconductor chips and substrate materials with thinning of substrates. As an approach for solving this problem, the functional polymer materials themselves for use in substrate materials are required to have lower thermal expansion and higher heat resistance. Furthermore, use of lead-free solder is promoted for the soldering of printed circuit boards, in consideration of human bodies and environments. In response to this, the functional polymer materials themselves are also required to have lower thermal expansion and higher heat resistance because of being capable of resisting a reflow step at a high temperature.

Conventional functional polymer materials may be allowed to contain a halogen atom or a phosphorus atom from the viewpoint of enhancing the flame retardancy of the functional polymer materials. However, the halogen atom has the possibility of generating halogen gases, which might cause environmental pollution, during combustion. In addition, the halogen atom reduces the insulating properties of final products. Also, the phosphorus atom often reduces the required properties (heat resistance, moisture resistance, and low water-absorbing property, etc.) except for flame retardancy. Accordingly, there is also a demand for improving the flame retardancy of the functional polymer materials without containing a halogen atom and a phosphorus atom.

A prepreg may be used when producing a laminate for use in printed circuit boards, etc. A prepreg may be produced by, first, dissolving an uncured monomer, which is a precursor of a functional polymer material, in a solvent such as methyl ethyl ketone to prepare varnish, impregnating glass fiber with the varnish, and drying the varnish. Therefore, there is also a demand for improving the solvent solubility of the monomers.

In the field of semiconductor sealing materials, studies have been actively conducted to replace silicon (Si) semiconductor devices with wide-gap semiconductors such as silicon carbide (SiC) semiconductors with the aim of reduction in power loss (energy saving). The SiC semiconductors are more chemically stable than the Si semiconductors and therefore permit operation at a high temperature exceeding 200° C., and it is also hoped that the apparatus size is reduced. In response to the replacement, compositions comprising functional polymer materials for use in sealing materials are required to have heat resistance, low thermal expansion, and heat resistance at high temperatures over a long period (hereinafter, referred to as "long-term heat resistance"), etc.

In order to obtain a hardened product of a cyanate ester compound alone which possesses low thermal expansion and heat resistance, use of a bifunctional cyanatophenyl-based cyanate ester compound in which a hydrogen atom of a methylene group that bonds cyanatophenyl groups is replaced by a particular alkyl group (1,1-bis(4-cyanatophenyl)isobutane) has been proposed (see Patent Document 1).

In order to obtain a hardened product of a cyanate ester compound alone which possesses flame retardancy and/or heat resistance, the use of a cyanate ester compound containing an isocyanuric acid skeleton (see Patent Document 2), a cyanate ester compound containing a triazine skeleton (see Patent Document 3), a bifunctional cyanatophenyl-based cyanate ester compound in which a hydrogen atom of a methylene group that bonds cyanatophenyl groups is replaced by a biphenyl group (see Patent Document 4), or a cyanation product of a phenol-modified xylene formaldehyde resin (see Patent Document 5); and a combination of a trifunctional cyanatophenyl-based (trisphenolalkane-based) cyanate ester compound and a bifunctional cyanatophenyl-based cyanate ester compound (see Patent Document 6) or a combination of a bisphenol A-based cyanate ester compound and an imide skeleton-containing cyanate ester compound (see Patent Document 7) have been proposed.

A composition containing a novolac-based cyanate, a novolac-based phenol resin, and an inorganic filler has been proposed as a composition which has heat resistance and high-temperature heat resistance over a long period (long-term heat resistance) and in which a cyanate ester compound is used (Patent Document 8).

CITATION LIST

Patent Documents

Patent Document 1: International Publication No. WO 2012/057144
Patent Document 2: Japanese Patent Publication No. 4654770
Patent Document 3: Japanese Patent Application Laid-Open No. 2012-036114
Patent Document 4: Japanese Patent Publication No. 5104312
Patent Document 5: International Publication No. WO 2013/021869
Patent Document 6: Japanese Patent Publication No. 2613056
Patent Document 7: Japanese Patent Application Laid-Open No. 2010-180147
Patent Document 8: Japanese Patent Application Laid-Open No. 2013-053218

SUMMARY OF INVENTION

Technical Problem

However, for the bifunctional cyanatophenyl-based cyanate ester compound, the flame retardancy (persistency at high temperatures) is reduced by replacing hydrogen of the methylene group that bonds cyanatophenyl groups with an alkyl group as described in Patent Document 1. Moreover, there is no description regarding flame retardancy and long-term heat resistance in Patent Document 1. There is no description regarding the coefficiency of thermal expansion, long-term heat resistance, and/or solvent solubility in Patent Documents 2 to 7. Furthermore, the duration of the test of long-term heat resistance in Patent Document 8 is about 50 hours (250° C.) and is not a sufficient test time. Moreover, there is no description regarding the coefficiency of thermal expansion and solvent solubility in Patent Document 8.

After all, a practical hardened product of a cyanate ester compound that possesses low thermal expansion, flame retardancy, and heat resistance at high levels has not yet been obtained by using a cyanate ester compound having solvent solubility. Accordingly, an object of the present invention is to provide a novel cyanate ester compound which has excellent solvent solubility and from which a hardened product having a low coefficiency of thermal expansion and excellent flame retardancy and heat resistance can be obtained, and a curable resin composition and the like containing the compound.

Solution to Problem

The present inventors found that a cyanate ester compound obtained by cyanating a specific resin has excellent solvent solubility and that a curable resin composition containing such a cyanate ester compound can achieve a hardened product or the like having a low coefficiency of thermal expansion and excellent flame retardancy and heat resistance, and arrived at the present invention. That is to say, the present invention is as set forth below.

[1]

A cyanate ester compound having one or more structures selected from the group consisting of structures represented by the following formula (1), formula (2), and formula (5):

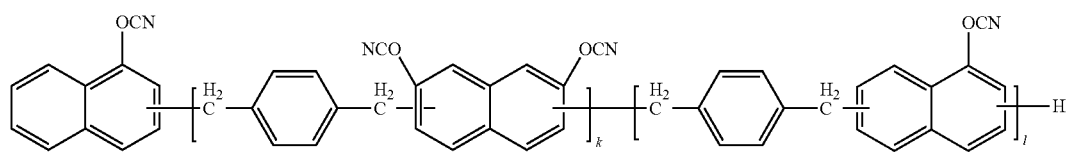

(1)

wherein k represents an integer of 1 or larger, and l represents an integer of 0 or larger; the compound may be a mixture of compounds differing from each other in k and l; and arrangement of repeating units is arbitrary;

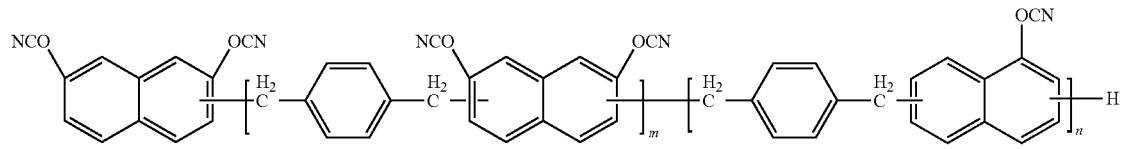

(2)

wherein m and n represent an integer of 0 or larger, and at least one is 1 or larger;
the compound may be a mixture of compounds differing from each other in m and n;
and arrangement of repeating units is arbitrary; and

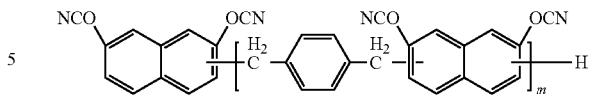

(5)

wherein m represents an integer of 0 or larger; and the compound may be a mixture of compounds differing from each other in m.

[2]

A cyanate ester compound obtained by cyanating one or more resins selected from the group consisting of naphthol-dihydroxynaphthalene aralkyl resins and dihydroxynaphthalene aralkyl resins.

[3]

The cyanate ester compound according to [1] obtained by cyanating one or more resins selected from the group consisting of naphthol-dihydroxynaphthalene aralkyl resins and dihydroxynaphthalene aralkyl resins.

[4]

The cyanate ester compound according to [2] or [3], wherein the naphthol-dihydroxynaphthalene aralkyl resin is obtained by reacting 1-naphthol, 2,7-dihydroxynaphthalene, and one or more selected from the group consisting of paraxylene glycol and 1,4-bis(methoxymethyl)benzene in the presence of an acidic catalyst, and the dihydroxynaphthalene aralkyl resin is obtained by reacting 2,7-dihydroxynaphthalene and one or more selected from the group consisting of paraxylene glycol and 1,4-bis(methoxymethyl)benzene in the presence of an acidic catalyst.

[5]

The cyanate ester compound according to any one of [1] to [4], wherein the cyanate ester compound has a weight-average molecular weight Mw of 100 to 5000.

[6]

A curable resin composition comprising a cyanate ester compound according to any one of [1] to [5].

[7]

The curable resin composition according to [6], further comprising one or more selected from the group consisting of a cyanate ester compound other than the cyanate ester compound, a maleimide compound, a phenol resin, an epoxy resin, an oxetane resin, a benzoxazine compound, and a compound having a polymerizable unsaturated group.

[8]

A hardened product obtained by curing a curable resin composition according to [6] or [7].

[9]

A prepreg for a structural material comprising:
a base material, and
a curable resin composition according to [6] or [7] with which the base material is impregnated or coated.

[10]

A sealing material, comprising a curable resin composition according to [6] or

[11]

A fiber-reinforced composite material comprising a curable resin composition according to [6] or [7].

[12]

An adhesive comprising a curable resin composition according to [6] or [7].

Advantageous Effects of Invention

The present invention can provide a novel cyanate ester compound which has excellent solvent solubility and from which a hardened product having a low coefficiency of thermal expansion and excellent flame retardancy and heat resistance is obtained, and a curable resin composition and the like containing the compound.

DESCRIPTION OF EMBODIMENTS

Figure 1:
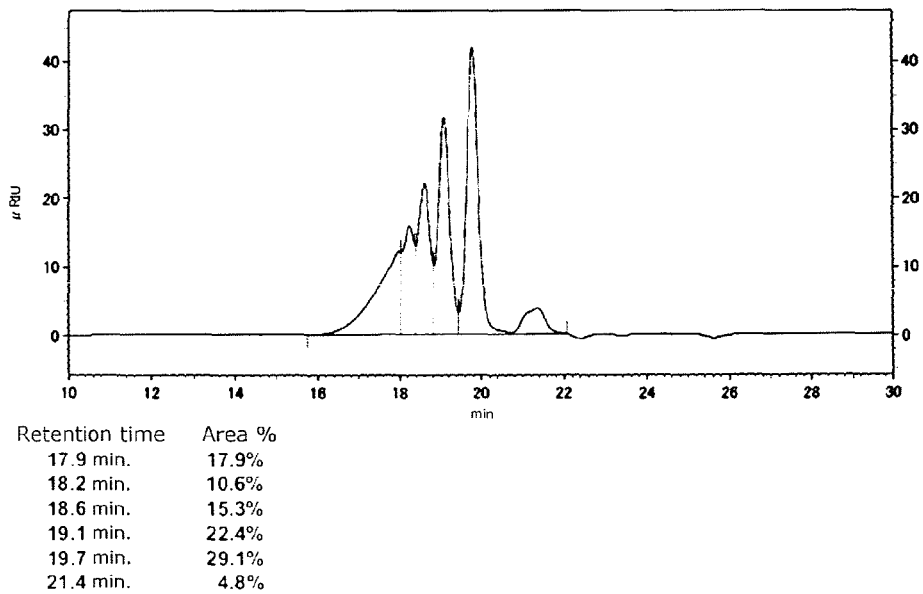
FIG. 1 shows a GPC chart of a naphthol-dihydroxynaphthalene aralkyl resin obtained in an Example.

Hereinafter, the mode for carrying out the present invention (hereinafter, simply referred to as the "present embodiment") will be described in detail in reference to the drawings as necessary, but the present invention is not limited to the present embodiment below. Various changes or modifications can be made to the present invention without departing from the spirit of the present invention.

The cyanate ester compound of the present embodiment is a cyanate ester compound obtained by cyanating one or more resins selected from the group consisting of naphthol-dihydroxynaphthalene aralkyl resins and dihydroxynaphthalene aralkyl resins (hereinafter these may be collectively referred to as "naphthol-dihydroxynaphthalene aralkyl resins and the like"). The curable resin composition of the present embodiment is a curable resin composition containing the cyanate ester compound.

Moreover, in another aspect of the present embodiment, a hardened product obtained by curing the curable resin composition as well as a sealing material, a fiber-reinforced composite material, and an adhesive containing the curable resin composition are also provided.

<Naphthol-Dihydroxynaphthalene Aralkyl Resin and the Like>

A naphthol-dihydroxynaphthalene aralkyl resin and the like that serve as starting materials of the cyanate ester compound of the present embodiment can be produced by the method described in, for example, Japanese Patent Publication No. H7-45557 or Japanese Patent Application Laid-Open No. 2014-9336, but the method is not particularly limited thereto. Specifically, the naphthol-dihydroxynaphthalene aralkyl resin can be obtained by reacting 1-naphthol, 2,7-dihydroxynaphthalene, and one or more selected from the group consisting of paraxylene glycol and 1,4-bis(methoxymethyl)benzene in the presence of an acidic catalyst. The dihydroxynaphthalene aralkyl resin can be obtained by reacting 2,7-dihydroxynaphthalene and one or more selected from the group consisting of paraxylene glycol and 1,4-bis(methoxymethyl)benzene in the presence of an acidic catalyst.

Examples of the acidic catalyst for use in the production of the naphthol-dihydroxynaphthalene aralkyl resin and the like include commonly used acidic catalysts, such as mineral acids such as hydrochloric acid, sulfuric acid, and phosphoric acid; organic acids such as oxalic acid, toluenesulfonic acid, and acetic acid; heteropoly acids such as tungstic acid; activated clay, inorganic acids, stannic chloride, zinc chloride, and ferric chloride; or other organic and inorganic acid salts that exhibit acidity. One of these acidic catalysts is used alone, or two or more are used in combination.

The amount of the acidic catalyst used is preferably 0.005 to 2.0 mol, more preferably 0.01 to 1.1 mol, based on 1 mol of the hydroxy groups of 1-naphthol and 2,7-dihydroxynaphthalene in total, or 1 mol of the hydroxy groups of 2,7-dihydroxynaphthalene in the case of not using 1-naphthol. An amount of the catalyst used of 0.005 mol or larger is preferred because there are advantages such that the reaction progresses more promptly, the reaction can be carried out at lower temperatures, and the reaction more reliably progresses to the end. An amount of the catalyst used of 2.0 mol or smaller is preferred because labor in post-treatment such as neutralization and purification can be reduced.

If necessary, an inert solvent can also be used in the reaction. Examples of the solvent include alcohol solvents such as methanol, ethanol, propanol, and isopropanol; aromatic hydrocarbon solvents such as toluene and xylene; and ketone solvents such as methyl isobutyl ketone (MIBK), cyclohexanone, cyclopentanone, and methyl ethyl ketone. One of these solvents can be used alone, or two or more can be used in combination. When a solvent is used, the amount of the solvent used is preferably 5 to 500 parts by mass, more preferably 10 to 400 parts by mass, based on 100 parts by mass of 1-naphthol and 2,7-dihydroxynaphthalene in total, or 100 parts by mass of 2,7-dihydroxynaphthalene in the case of not using 1-naphthol.

The reaction temperature in the reaction is preferably 0 to 300° C., more preferably 40 to 230° C.

The reaction time in the reaction is preferably 1 to 200 hours, more preferably 2 to 150 hours.

In the reaction, the total amount of 1-naphthol and 2,7-dihydroxynaphthalene used, or the total amount of 2,7-dihydroxynaphthalene used in the case of not using 1-naphthol, is preferably 1.2 to 20 mol, more preferably 1.5 to 10 mol, based on 1 mol of the total amount of paraxylene glycol and 1,4-bis(methoxymethyl)benzene. When the amount is 1.2 mol or larger, the softening point of the produced naphthol-dihydroxynaphthalene aralkyl resin or dihydroxynaphthalene aralkyl resin can be more suitably lowered, and the resin can be more easily removed from the reactor after reaction. When the amount is 20 mol or smaller, a decrease of one or more structures selected from the group consisting of structures represented by the following formulae (3), (4), and (5) can be more suppressed, and a reduction of heat resistance can be more prevented.

unreacted paraxylene glycol and 1,4-bis(methoxymethyl)benzene, unreacted 1-naphthol, unreacted 2,7-dihydroxynaphthalene, the acidic catalyst, reaction by-products, etc. Therefore, it is preferred that the compound of interest is separated and purified by a method routinely used, for example, a separation approach such as neutralization, washing with water, filtration, concentration, extraction, crystallization, recrystallization, column chromatography, or a combination of these separation approaches.

The naphthol-dihydroxynaphthalene aralkyl resin and the like according to the present embodiment that can be obtained by the production methods described above may have, but are not particularly limited to, one or more structures selected from the group consisting of structures represented by the following formulae (3), (4), and (6):

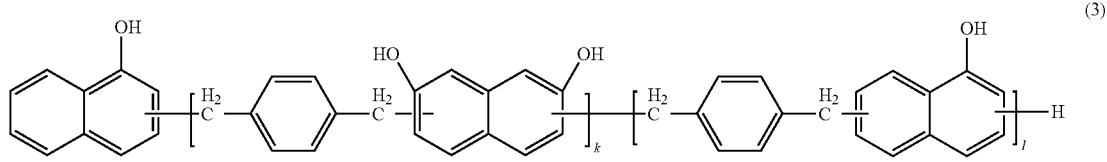

(3)

Among the reactions described above, the reaction to obtain the naphthol-dihydroxynaphthalene aralkyl resin is performed by optionally adding an acidic catalyst to a mixture of 1-naphthol, 2,7-dihydroxynaphthalene, one or more selected from the group consisting of paraxylene glycol and 1,4-bis(methoxymethyl)benzene, and optionally a solvent, and heating the mixture. The reaction can also be performed by slowly adding one or more selected from the group consisting of paraxylene glycol and 1,4-bis(methoxymethyl)benzene to a mixture, which is being heated, of 1-naphthol, 2,7-dihydroxynaphthalene, an acid catalyst, and optionally a solvent. Among the reactions described above, the reaction to obtain the dihydroxynaphthalene aralkyl resin is performed by optionally adding an acidic catalyst to a mixture of 2,7-dihydroxynaphthalene, one or more selected from the group consisting of paraxylene glycol and 1,4-bis(methoxymethyl)benzene, and optionally a solvent, and heating the mixture. The reaction can also be performed by slowly adding one or more selected from the group consisting of paraxylene glycol and 1,4-bis(methoxymethyl)benzene to a mixture, which is being heated, of 2,7-dihydroxynaphthalene, an acid catalyst, and optionally a solvent. These reactions may be performed with stirring, may be performed in air or in an inert gas (such as nitrogen, helium, or argon) atmosphere, and may be performed under normal pressure or high pressure. The progression of the reaction can be confirmed (or monitored) by high-performance liquid chromatography (HPLC), thin-layer chromatography (TLC), or the like.

After the completion of the reaction, the reaction mixture contains one or more selected from the group consisting of wherein k represents an integer of 1 or larger, and l represents an integer of 0 or larger; the compound may be a mixture of compounds differing from each other in k and l; and arrangement of repeating units is arbitrary;

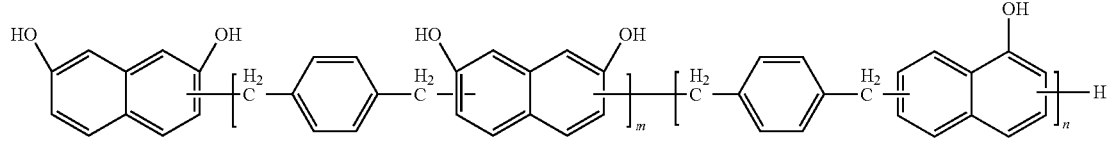

(4)

wherein m and n represent an integer of 0 or larger, and at least one is 1 or larger;
the compound may be a mixture of compounds differing from each other in m and n;
and arrangement of repeating units is arbitrary; and

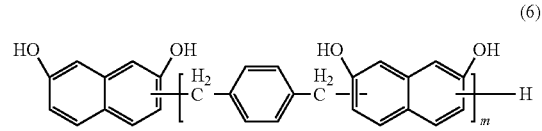

(6)

wherein m represents an integer of 0 to 20; and the compound may be a mixture of compounds differing from each other in m.

<Cyanate Ester Compound>

The cyanate ester compound of the present embodiment is obtained by cyanating the hydroxy groups of the naphthol-dihydroxynaphthalene aralkyl resin or the like (hereinafter, this step is also referred to as a "cyanation step"). The cyanation method is not particularly limited, and known methods can be applied. More specifically, the cyanate ester compound of the present embodiment can be obtained by a method in which the naphthol-dihydroxynaphthalene aralkyl resin or the like is reacted with a cyanogen halide in the presence of a basic compound in a solvent; a method in which the naphthol-dihydroxynaphthalene aralkyl resin or the like is reacted with a cyanogen halide in the presence of a base in a solvent such that the cyanogen halide is always present in excess of the base (see U.S. Pat. No. 3,553,244); a method in which a tertiary amine used as a base in excess of a cyanogen halide is added to the naphthol-dihydroxynaphthalene aralkyl resin or the like in the presence of a solvent and thereafter the cyanogen halide is dropped or both the cyanogen halide and the tertiary amine are dropped (see Japanese Patent No. 3319061); a method in which the naphthol-dihydroxynaphthalene aralkyl resin or the like, a trialkylamine, and a cyanogen halide are reacted in a continuous plug flow mode (see Japanese Patent No. 3905559); a method in which a tert-ammonium halide produced as a by-product in reacting the naphthol-dihydroxynaphthalene aralkyl resin or the like with a cyanogen halide in the presence of a tert-amine in a nonaqueous solution is treated with a cation and anion exchange pair (see Japanese Patent No. 4055210); a method which involves simultaneously adding a tertiary amine and a cyanogen halide to the naphthol-dihydroxynaphthalene aralkyl resin or the like in the presence of a solvent separable from water, reacting the mixture, then washing the reaction mixture with water, separating the reaction mixture into aqueous and organic layers, and purifying the reaction product from the obtained solution by precipitation using a secondary or tertiary alcohol or a hydrocarbon as a poor solvent (see Japanese Patent No. 2991054); a method which involves reacting the naphthol-dihydroxynaphthalene aralkyl resin or the like, a cyanogen halide, and a tertiary amine under acidic conditions in a two-phase solvent of water and an organic solvent (Japanese Patent No. 5026727); or the like.

When the method is used which involves reacting the naphthol-dihydroxynaphthalene aralkyl resin or the like described above with a cyanogen halide in the presence of a basic compound in a solvent, the naphthol-dihydroxynaphthalene aralkyl resin or the like serving as a reaction substrate may be dissolved in advance in either of a cyanogen halide solution or a basic compound solution, and then the cyanogen halide solution and the basic compound solution may be contacted with each other.

Examples of the method for contacting the cyanogen halide solution and the basic compound solution with each other (hereinafter, it may be simply referred to as a "contact method") include a method (A) of pouring the basic compound solution to the cyanogen halide solution mixed by stirring, a method (B) of pouring the cyanogen halide solution to the basic compound solution mixed by stirring, and a method (C) of supplying the cyanogen halide solution and the basic compound solution either alternately in a continuous manner or at the same time. Among the methods (A), (B), and (C), the method (A) is preferred because a side reaction is more suppressed, and a cyanate ester compound having a higher purity can be obtained at a high yield.

The method for bringing a cyanogen halide solution into contact with a basic compound solution may be performed either in a semibatch form or in a continuous flow form.

Since the reaction can be completed with no remaining hydroxy groups contained in the naphthol-dihydroxynaphthalene aralkyl resin or the like, and a higher-purity cyanate ester compound can be obtained at a high yield when the method (A) is particularly used, it is preferable that a basic compound is poured in portions. The number of such portions is not particularly limited. It is preferably 1 to 5 times. Either a single identical basic compound or different basic compounds may be used for each division.

Examples of the cyanogen halide used in the present embodiment include cyanogen chloride and cyanogen bromide. The cyanogen halide may be a cyanogen halide obtained by a production method known in the art such as a method of reacting hydrogen cyanide or metal cyanide with halogen, or may be a commercially available product. Alternatively, a reaction solution containing the cyanogen halide obtained by reacting hydrogen cyanide or metal cyanide with halogen may be used directly.

The amount of cyanogen halide used in the cyanation step of the present embodiment based on the naphthol-dihydroxynaphthalene aralkyl resin or the like is preferably 0.5 to 5 mol, more preferably 1.0 to 3.5 mol, based on 1 mol of the hydroxy groups of the naphthol-dihydroxynaphthalene aralkyl resin or the like. Accordingly, the yield of the cyanate ester compound can be more increased while further lessening the remaining unreacted naphthol-dihydroxynaphthalene aralkyl resin or the like.

Examples of the solvent that can be contained in the cyanogen halide solution include ketone solvents such as acetone, methyl ethyl ketone, methyl isobutyl ketone, cyclohexanone, and cyclopentanone; aliphatic hydrocarbon solvents such as n-hexane, cyclohexane, and isooctane; aromatic hydrocarbon solvents such as benzene, toluene, and xylene; ether solvents such as diethyl ether, dimethyl cellosolve, diglyme, tetrahydrofuran, methyltetrahydrofuran, dioxane, and tetraethylene glycol dimethyl ether; halogenated hydrocarbon solvents such as dichloromethane, chloroform, carbon tetrachloride, dichloroethane, trichloroethane, chlorobenzene, and bromobenzene; alcohol solvents such as methanol, ethanol, isopropanol, methyl cellosolve, and propylene glycol monomethyl ether; aprotic polar solvents such as N,N-dimethylformamide, N-methylpyrrolidone, 1,3-dimethyl-2-imidazolidone, and dimethyl sulfoxide; nitrile solvents such as acetonitrile and benzonitrile; nitro solvents such as nitromethane and nitrobenzene; ester solvents such as ethyl acetate and ethyl benzoate; and a water solvent. These can be used singly or in combination of two or more, depending on the type of a reaction substrate.

Any of organic and inorganic bases can be used as the basic compound for use in the cyanation step of the present embodiment. These are used singly or in combination of two or more.

The organic base is not particularly limited, and from the viewpoint of obtaining the compound of interest at a higher yield, tertiary amines such as trimethylamine, triethylamine, tri-n-butylamine, triamylamine, diisopropylethylamine, diethyl-n-butylamine, methyl-di-n-butylamine, methyl-ethyl-n-butylamine, dodecyldimethylamine, tribenzylamine, triethanolamine, N,N-dimethylaniline, N,N-diethylaniline, di phenylmethylamine, pyridine, diethylcyclohexylamine, tricyclohexylamine, 1,4-diazabicyclo[2.2.2]octane, 1,8-diazabicyclo[5.4.0]-7-undecene and 1,5-diazabicyclo[4.3.0]-5-nonene are preferred. Among these organic bases, trimethylamine, triethylamine, tri-n-butylamine, and diisopropylethylamine are more preferred, and triethylamine is particularly preferred, from the viewpoint of obtaining the compound of interest at a yet higher yield.

The amount of the organic base used is preferably 0.1 to 8 mol, more preferably 1.0 to 3.5 mol, based on 1 mol of the hydroxy groups of the naphthol-dihydroxynaphthalene aralkyl resin or the like. This is because the yield of the cyanate ester compound can be more increased while further lessening the remaining unreacted naphthol-dihydroxynaphthalene aralkyl resin or the like.

The inorganic base is not particularly limited, and is preferably a hydroxide of an alkali metal from the viewpoint of obtaining the compound of interest at a higher yield. Examples of the hydroxides of alkali metals include, but are not particularly limited to, sodium hydroxide, potassium hydroxide, and lithium hydroxide generally used industrially. Among these, sodium hydroxide is particularly preferred because of being inexpensively available.

The amount of the inorganic base used is preferably 1.0 to 5.0 mol, more preferably 1.0 to 3.5 mol, based on 1 mol of the hydroxy groups of the naphthol-dihydroxynaphthalene aralkyl resin or the like. This is because the yield of the cyanate ester compound can be more increased while further lessening the remaining unreacted naphthol-dihydroxynaphthalene aralkyl resin or the like.

In the reaction of the present embodiment, the basic compound can be dissolved in a solvent and used as a solution, as mentioned above. For example, an organic solvent or water can be used as the solvent.

In the case of dissolving the naphthol-dihydroxynaphthalene aralkyl resin or the like in the basic compound solution, the amount of the solvent used, which can be contained in the basic compound solution, is preferably 0.1 to 100 parts by mass, more preferably 0.5 to 50 parts by mass, based on 1 part by mass of the naphthol-dihydroxynaphthalene aralkyl resin or the like. In the case of not dissolving the naphthol-dihydroxynaphthalene aralkyl resin or the like in the basic compound solution, the amount of the solvent used is preferably 0.1 to 100 parts by mass, more preferably 0.25 to 50 parts by mass, based on 1 part by mass of the basic compound.

The organic solvent for dissolving the basic compound is preferably used when the basic compound is an organic base. Examples of such organic solvents include ketone solvents such as acetone, methyl ethyl ketone, and methyl isobutyl ketone; aromatic hydrocarbon solvents such as benzene, toluene, and xylene; ether solvents such as diethyl ether, dimethyl cellosolve, diglyme, tetrahydrofuran, methyltetrahydrofuran, dioxane, and tetraethylene glycol dimethyl ether; halogenated hydrocarbon solvents such as dichloromethane, chloroform, carbon tetrachloride, dichloroethane, trichloroethane, chlorobenzene, and bromobenzene; alcohol solvents such as methanol, ethanol, isopropanol, methyl cellosolve, and propylene glycol monomethyl ether; aprotic polar solvents such as N,N-dimethylformamide, N-methylpyrrolidone, 1,3-dimethyl-2-imidazolidone, and dimethyl sulfoxide; nitrile solvents such as acetonitrile and benzonitrile; nitro solvents such as nitromethane and nitrobenzene; ester solvents such as ethyl acetate and ethyl benzoate; and aliphatic hydrocarbon solvents such as cyclohexane. The organic solvent can be appropriately selected according to the basic compound, the reaction substrate, and the solvent for use in the reaction. One type of organic solvent can be used alone, or two or more types of organic solvents can be used in combination.

The water for dissolving the basic compound is preferably used when the basic compound is an inorganic base. The water is not particularly limited and may be tap water, may be distilled water, or may be deionized water. Distilled water and deionized water with a low impurity content are preferred from the viewpoint of more efficiently obtaining the cyanate ester compound of interest.

When the solvent contained in the basic compound solution is water, it is preferred to use a catalytic amount of an organic base as a surfactant, from the viewpoint of securing a more sufficient reaction rate. Among others, a tertiary amine less likely to cause side reaction is preferred. The tertiary amine may be any of alkylamine, arylamine, and cycloalkylamine. Specific examples thereof include trimethylamine, triethylamine, tri-n-butylamine, triamylamine, diisopropylethylamine, diethyl-n-butylamine, methyl-di-n-butylamine, methylethyl-n-butylamine, dodecyldimethylamine, tribenzylamine, triethanolamine, N,N-dimethylaniline, N,N-diethylaniline, diphenylmethylamine, pyridine, diethylcyclohexylamine, tricyclohexylamine, 1,4-diazabicyclo[2.2.2]octane, 1,8-diazabicyclo[5.4.0]-7-undecene, and 1,5-diazabicyclo[4.3.0]-5-nonene. Among these tertiary amines, trimethylamine, triethylamine, tri-n-butylamine, and diisopropylethylamine are more preferred, and triethylamine is particularly preferred, from the viewpoint of solubility in water and from the viewpoint of obtaining the compound of interest at a higher yield. One of these tertiary amines is used alone, or two or more are used in combination.

The total amount of the solvents for use in the cyanation step of the present embodiment is preferably 2.5 to 100 parts by mass based on 1 part by mass of the naphthol-dihydroxynaphthalene aralkyl resin or the like from the viewpoint of more uniformly dissolving the naphthol-dihydroxynaphthalene aralkyl resin or the like and more efficiently producing the cyanate ester compound.

In the cyanation step of the present embodiment, the pH of the reaction solution is not particularly limited, and the reaction is preferably performed with the pH kept at lower than 7. When the pH is kept at lower than 7, the formation of by-products such as imidocarbonate and polymerization products of the cyanate ester compound is more suppressed so that the cyanate ester compound can be more efficiently produced. A method of adding an acid to the reaction solution is preferred for keeping the pH of the reaction solution at lower than 7. As methods of adding an acid to the reaction solution, a method involving adding an acid to the cyanogen halide solution immediately before the cyanation step and a method involving adding an acid to the reaction system while appropriately measuring the pH of the reaction solution using a pH meter during the reaction to keep the pH at lower than 7 are more preferred.

Examples of the acid for use in this operation include inorganic acids such as hydrochloric acid, nitric acid, sulfuric acid, and phosphoric acid; and organic acids such as acetic acid, lactic acid, and propionic acid.

The reaction temperature in the cyanation step of the present embodiment is preferably −20 to +50° C., more preferably −15 to 15° C., further preferably −10 to 10° C., from the viewpoint of more suppressing the formation of by-products such as imidocarbonate, polymerization products of the cyanate ester compound, and dialkyl cyanamide, from the viewpoint of more suppressing the condensation of the reaction solution, and, in the case of using cyanogen chloride as the cyanogen halide, from the viewpoint of more suppressing the volatilization of the cyanogen chloride.

The reaction pressure in the cyanation step of the present embodiment may be normal pressure, or may be high pressure, i.e., a pressure higher than normal pressure. If necessary, an inert gas such as nitrogen, helium, or argon may be passed through the reaction system. The reaction time is not particularly limited, and the pouring time when the contact method is the methods (A) and (B), and the contact time when the contact method is the method (C), are preferably 1 minute to 20 hours, more preferably 3 minutes to 10 hours. It is further preferred to then stir the reaction solution for 10 minutes to 10 hours with the reaction temperature maintained.

When the reaction conditions fall within the range as described above, the cyanate ester compound of interest is obtained more economically and more industrially.

In the cyanation step, the degree of progression of the reaction can be analyzed by liquid chromatography or IR spectroscopy, etc. Volatile components such as by-products dicyanogen and dialkyl cyanamide can be analyzed by gas chromatography.

wherein k represents an integer of 1 or larger, and l represents an integer of 0 or larger; the compound may be a mixture of compounds differing from each other in k and l; arrangement of repeating units is arbitrary; the upper limit of k is not particularly limited, and is preferably 20 or smaller from the viewpoint of more effectively and reliably demonstrating the action and effect provided by the present invention; and from the same viewpoint, the upper limit of l is preferably 20 or smaller; and

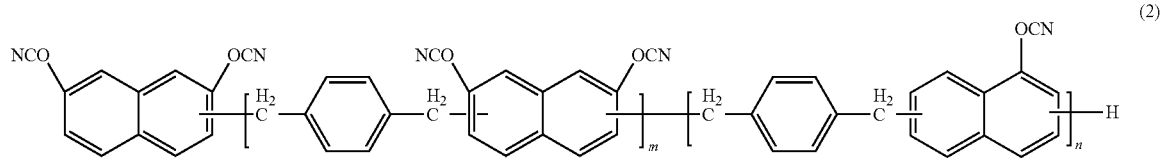

(2)

After the completion of the reaction, the cyanate ester compound of interest can be isolated by usual aftertreatment operation that can be performed after synthesizing a conventional cyanate ester compound and, if desired, separation and purification operation. Specifically, an organic solvent phase containing the cyanate ester compound can be separated from the reaction solution and washed with water, followed by concentration, precipitation, or crystallization. Alternatively, the separated organic solvent phase may be washed with water, followed by solvent substitution. For the washing, a method using an acidic aqueous solution such as dilute hydrochloric acid in place of water can also be adopted in order to remove an excess of amines. The thoroughly washed reaction solution can be dried by a general method using sodium sulfate, magnesium sulfate, or the like in order to remove water from the reaction solution. For the concentration and the solvent substitution, the organic solvent is distilled off by heating to a temperature of 90° C. or lower under reduced pressure in order to suppress the polymerization of the cyanate ester compound. For the precipitation or the crystallization, a solvent having a low degree of dissolution of the cyanate ester compound can be used. For example, a method of adding dropwise an ether solvent, a hydrocarbon solvent (e.g., hexane), or an alcohol solvent to the reaction solution or a method of pouring the reaction solution to the solvent can be adopted. A method of washing the concentrate of the reaction solution or precipitated crystals with an ether solvent, a hydrocarbon solvent (e.g., hexane), or an alcohol solvent can be adopted in order to wash the obtained crude product. Crystals obtained by the concentration of the reaction solution may be redissolved and then recrystallized. The crystallization may be performed by the simple concentration or cooling of the reaction solution.

The cyanate ester compound obtained by the production methods described above has, but is not particularly limited to, one or more structures selected from the group consisting of structures represented by the following formulae (1), (2), and (5):

wherein m and n represent an integer of 0 or larger, and at least one is 1 or larger;
the compound may be a mixture of compounds differing from each other in m and n;
arrangement of repeating units is arbitrary; the upper limit of m is not particularly limited, and is preferably 20 or smaller from the viewpoint of more effectively and reliably demonstrating the action and effect provided by the present invention; and from the same viewpoint, the upper limit of n is preferably 20 or smaller; and

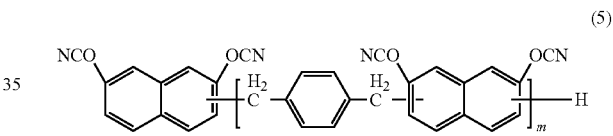

(5)

wherein m represents an integer of 0 or larger; the compound may be a mixture of compounds differing from each other in m; the upper limit of m is not particularly limited, and is preferably 20 or smaller from the viewpoint of more effectively and reliably demonstrating the action and effect provided by the present invention.

The weight-average molecular weight Mw of the cyanate ester compound of the present embodiment is not particularly limited, and is preferably 100 to 5000, more preferably 200 to 3500, and further preferably 200 to 3000. The weight-average molecular weight Mw is measured by the method described in the Examples.

The obtained cyanate ester compound can be identified by a method known in the art such as NMR. The purity of the cyanate ester compound can be analyzed by liquid chromatography or IR spectroscopy, etc. Volatile components such as by-products (e.g., dialkyl cyanamide) or residual solvents in the cyanate ester compound can be quantitatively analyzed by gas chromatography. Halogen compounds remain-

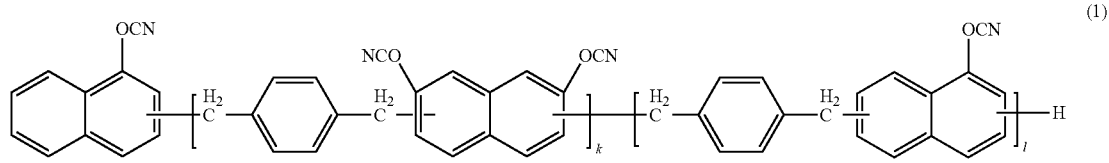

(1)

ing in the cyanate ester compound can be identified using a liquid chromatography-mass spectrometer and can also be quantitatively analyzed by potentiometric titration using a silver nitrate solution or by ion chromatography after decomposition by a combustion method. The polymerization reactivity of the cyanate ester compound can be evaluated on the basis of the time to gel by a hot plate method or a torque measurement method.

<Curable Resin Composition>

The curable resin composition of the present embodiment contains the cyanate ester compound. The curable resin composition may optionally contain one or more selected from the group consisting of an cyanate ester compound other than the cyanate ester compound described above (hereinafter referred to as a "further cyanate ester compound"), a maleimide compound, a phenol resin, an epoxy resin, an oxetane resin, a benzoxazine compound, and a compound having a polymerizable unsaturated group, as long as the desired properties are not impaired.

The further cyanate ester compound is not particularly limited as long as it is a compound that has within the molecule an aromatic moiety substituted with at least one cyanate group and that is not obtained by cyanating the naphthol-dihydroxynaphthalene aralkyl resin or the like. Examples include those represented by the following formula (7):

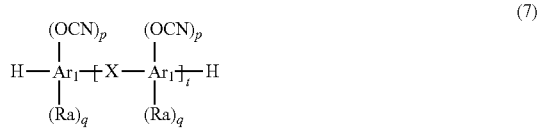

(7)

wherein $Ar_1$ represents a benzene ring, a naphthalene ring, or two benzene rings bonded by a single bond, and a plurality of $Ar_1$ if present, may be mutually the same or different; Ra each independently represents a hydrogen atom, an alkyl group having 1 to 6 carbon atoms, an aryl group having 6 to 12 carbon atoms, an alkoxy group having 1 to 4 carbon atoms, or a group in which an alkyl group having 1 to 6 carbon atoms and an aryl group having 6 to 12 carbon atoms are bonded; the aromatic ring in Ra may have a substituent, and the substituent in $Ar_1$ and Ra can be at any position; p represents the number of cyanato groups bonded to $Ar_1$ and each p is independently an integer of 1 to 3; q represents the number of Ra bonded to $Ar_1$ and is 4-p when $Ar_1$ is a benzene ring, 6-p when $Ar_1$ is a naphthalene ring, and 8-p when $Ar_1$ is two benzene rings bonded by a single bond; t represents the average number of a repeat and is an integer of 0 to 50, and the further cyanate ester compound may be a mixture of compounds differing from each other in t; a plurality of X, if present, each independently represent a single bond, a divalent organic group having 1 to 50 carbon atoms (a hydrogen atom may be replaced by a heteroatom), a divalent organic group having 1 to 10 nitrogen atoms (e.g., —N—R—N— (wherein R represents an organic group)), a carbonyl group (—CO—), a carboxy group (—C(=O)O—), a carbonyl dioxide group (—OC(=O)O—), a sulfonyl group (—SO$_2$—), a divalent sulfur atom, or a divalent oxygen atom.

The alkyl group represented by Ra in formula (7) may have any of linear, branched, and cyclic structures (e.g., a cycloalkyl group). A hydrogen atom in the alkyl group, and in the aryl group represented by Ra, in formula (7) may be replaced by a halogen atom such as a fluorine atom or a chlorine atom, an alkoxy group such as a methoxy group or a phenoxy group, a cyano group, or the like.

Specific examples of the alkyl group include a methyl group, an ethyl group, a propyl group, an isopropyl group, a n-butyl group, an isobutyl group, a tert-butyl group, a n-pentyl group, a 1-ethylpropyl group, a 2,2-dimethylpropyl group, a cyclopentyl group, a hexyl group, a cyclohexyl group, and a trifluoromethyl group.

Specific examples of the aryl group include a phenyl group, a xylyl group, a mesityl group, a naphthyl group, a phenoxyphenyl group, an ethylphenyl group, an o-, m-, or p-fluorophenyl group, a dichlorophenyl group, a dicyanophenyl group, a trifluorophenyl group, a methoxyphenyl group, and an o-, m-, or p-tolyl group. Moreover examples of the alkoxy group include a methoxy group, an ethoxy group, a propoxy group, an isopropoxy group, a n-butoxy group, an isobutoxy group, and a tert-butoxy group.

Specific examples of the divalent organic group having 1 to 50 carbon atoms represented by X in formula (7) include alkylene groups such as a methylene group, an ethylene group, a trimethylene group, and a propylene group; cycloalkylene groups such as a cyclopentylene group, a cyclohexylene group, and a trimethylcyclohexylene group; and divalent organic groups having an aromatic ring, such as a biphenylylmethylene group, a dimethylmethylene-phenylene-dimethylmethylene group, a fluorenediyl group, and a phthalidodiyl group. A hydrogen atom in the divalent organic group may be replaced by a halogen atom such as a fluorine atom or a chlorine atom, an alkoxy group such as a methoxy group or a phenoxy group, a cyano group, or the like.

Examples of the divalent organic group having 1 to 10 nitrogen atoms represented by X in formula (7) include a group represented by —N—R—N—, an imino group, and a polyimide group.

Examples of the organic group represented by X in formula (7) also include divalent groups represented by the following formula (8) or the following formula (9):

(8)

wherein $Ar_2$ represents a benzenetetrayl group, a naphthalenetetrayl group, or a biphenyltetrayl group, and may be mutually the same or different when u is 2 or larger; Rb, Rc, Rf, and Rg each independently represent a hydrogen atom, an alkyl group having 1 to 6 carbon atoms, an aryl group having 6 to 12 carbon atoms, a trifluoromethyl group, or an aryl group having at least one phenolic hydroxy group; Rd and Re each independently represent any of a hydrogen atom, an alkyl group having 1 to 6 carbon atoms, an aryl group having 6 to 12 carbon atoms, an alkoxy group having 1 to 4 carbon atoms, or a hydroxy group; u represents an integer of 0 to 5; and

(9)

wherein Ar₃ represents a benzenetetrayl group, a naphthalenetetrayl group, or a biphenyltetrayl group, and may be mutually the same or different when v is 2 or larger; Ri and Rj each independently represent a hydrogen atom, an alkyl group having 1 to 6 carbon atoms, an aryl group having 6 to 12 carbon atoms, a benzyl group, an alkoxy group having 1 to 4 carbon atoms, a hydroxy group, a trifluoromethyl group, or an aryl group substituted with at least one cyanate group; v represents an integer of 0 to 5; and the compound may be a mixture of compounds differing from each other in v.

Furthermore, examples of X in formula (7) include divalent groups represented by the following formulae:

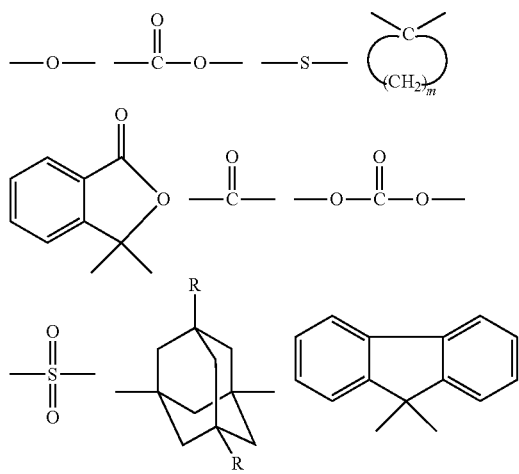

wherein m represents an integer of 4 to 7; and each R independently represents a hydrogen atom or an alkyl group having 1 to 6 carbon atoms.

Specific examples of Ar₂ in formula (8) and Ar_a in formula (9) include a benzenetetrayl group in which two carbon atoms shown in formula (8) or two oxygen atoms shown in formula (9) are bonded to 1,4-positions or 1,3-positions; a biphenyltetrayl group in which the above two carbon atoms or two oxygen atoms are bonded to 4,4'-positions, 2,4'-positions, 2,2'-positions, 2,3'-positions, 3,3'-positions, or 3,4'-positions; and a naphthalenetetrayl group in which the above two carbon atoms or two oxygen atoms are bonded to 2,6-positions, 1,5-positions, 1,6-positions, 1,8-positions, 1,3-positions, 1,4-positions, or 2,7-positions.

Examples of the alkyl group and the aryl group represented by Rb, Rc, Rd, Re, Rf, and Rg in formula (8) and Ri and Rj in formula (9) are the same as those in formula (7) above.

Specific examples of the cyanato-substituted aromatic compound represented by formula (7) above include cyanatobenzene, 1-cyanato-2-, 1-cyanato-3-, or 1-cyanato-4-methylbenzene, 1-cyanato-2-, 1-cyanato-3-, or 1-cyanato-4-methoxybenzene, 1-cyanato-2,3-, 1-cyanato-2,4-, 1-cyanato-2,5-, 1-cyanato-2,6-, 1-cyanato-3,4- or 1-cyanato-3,5-dimethylbenzene, cyanatoethylbenzene, cyanatobutylbenzene, cyanatooctylbenzene, cyanatononylbenzene, 2-(4-cyanatophenyl)-2-phenylpropane (4-α-cumylphenol cyanate), 1-cyanato-4-cyclohexylbenzene, 1-cyanato-4-vinylbenzene, 1-cyanato-2- or 1-cyanato-3-chlorobenzene, 1-cyanato-2,6-dichlorobenzene, 1-cyanato-2-methyl-3-chlorobenzene, cyanatonitrobenzene, 1-cyanato-4-nitro-2-ethylbenzene, 1-cyanato-2-methoxy-4-allylbenzene (eugenol cyanate), methyl(4-cyanatophenyl)sulfide, 1-cyanato-3-trifluoromethylbenzene, 4-cyanatobiphenyl, 1-cyanato-2- or 1-cyanato-4-acetylbenzene, 4-cyanatobenzaldehyde, 4-cyanatobenzoic acid methyl ester, 4-cyanatobenzoic acid phenyl ester, 1-cyanato-4-acetaminobenzene, 4-cyanatobenzophenone, 1-cyanato-2,6-di-tert-butylbenzene, 1,2-dicyanatobenzene, 1,3-dicyanatobenzene, 1,4-dicyanatobenzene, 1,4-dicyanato-2-tert-butylbenzene, 1,4-dicyanato-2,4-dimethylbenzene, 1,4-dicyanato-2,3,4-trimethylbenzene, 1,3-dicyanato-2,4,6-trimethylbenzene, 1,3-dicyanato-5-methylbenzene, 1-cyanato or 2-cyanatonaphthalene, 1-cyanato-4-methoxynaphthalene, 2-cyanato-6-methylnaphthalene, 2-cyanato-7-methoxynaphthalene, 2,2'-dicyanato-1,1'-binaphthyl, 1,3-, 1,4-, 1,5-, 1,6-, 1,7-, 2,3-, 2,6- or 2,7-dicyanatonaphthalene, 2,2'- or 4,4'-dicyanatobiphenyl, 4,4'-dicyanatooctafluorobiphenyl, 2,4'- or 4,4'-dicyanatodiphenylmethane, bis(4-cyanato-3,5-dimethylphenyl)methane, 1,1-bis(4-cyanatophenyl)ethane, 1,1-bis(4-cyanatophenyl)propane, 2,2-bis(4-cyanatophenyl)propane, 2,2-bis(4-cyanato-3-methyl phenyl)propane, 2,2-bis(2-cyanato-5-biphenylyl)propane, 2,2-bis(4-cyanatophenyl)hexafluoropropane, 2,2-bis(4-cyanato-3,5-dimethylphenyl)propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 2,2-bis(4-cyanatophenyl)butane, 2,2-bis(4-cyanatophenyl)pentane, 2,2-bis(4-cyanatophenyl)hexane, 2,2-bis(4-cyanatophenyl)-3-methylbutane, 2,2-bis(4-cyanatophenyl)-4-methylpentane, 2,2-bis(4-cyanatophenyl)-3,3-dimethylbutane, 3,3-bis(4-cyanatophenyl)hexane, 3,3-bis(4-cyanatophenyl)heptane, 3,3-bis(4-cyanatophenyl)octane, 3,3-bis(4-cyanatophenyl)-2-methylpentane, 3,3-bis(4-cyanatophenyl)-2-methylhexane, 3,3-bis(4-cyanatophenyl)-2,2-dimethylpentane, 4,4-bis(4-cyanatophenyl)-3-methylheptane, 3,3-bis(4-cyanatophenyl)-2-methylheptane, 3,3-bis(4-cyanatophenyl)-2,2-dimethylhexane, 3,3-bis(4-cyanatophenyl)-2,4-dimethylhexane, 3,3-bis(4-cyanatophenyl)-2,2,4-trimethylpentane, 2,2-bis(4-cyanatophenyl)-1,1,1,3,3,3-hexafluoropropane, bis(4-cyanatophenyl)phenylmethane, 1,1-bis(4-cyanatophenyl)-1-phenylethane, bis(4-cyanatophenyl)biphenylmethane, 1,1-bis(4-cyanatophenyl)cyclopentane, 1,1-bis(4-cyanatophenyl)cyclohexane, 2,2-bis(4-cyanato-3-isopropylphenyl)propane, 1,1-bis(3-cyclohexyl-4-cyanatophenyl)cyclohexane, bis(4-cyanatophenyl)diphenylmethane, bis(4-cyanatophenyl)-2,2-dichloroethylene, 1,3-bis[2-(4-cyanatophenyl)-2-propyl]benzene, 1,4-bis[2-(4-cyanatophenyl)-2-propyl]benzene, 1,1-bis(4-cyanatophenyl)-3,3,5-trimethylcyclohexane, 4-[bis(4-cyanatophenyl)methyl]biphenyl, 4,4-dicyanatobenzophenone, 1,3-bis(4-cyanatophenyl)-2-propen-1-one, bis(4-cyanatophenyl) ether, bis(4-cyanatophenyl)sulfide, bis(4-cyanatophenyl)sulfone, 4-cyanatobenzoic acid-4-cyanatophenyl ester (4-cyanatophenyl-4-cyanatobenzoate), bis-(4-cyanatophenyl)carbonate, 1,3-bis(4-cyanatophenyl)adamantane, 1,3-bis(4-cyanatophenyl)-5,7-dimethyladamantane, 1,3-bis(3-methyl-4-cyanatophenyl)-5,7-dimethyladamantane, 3,3-bis(4-cyanatophenyl)isobenzofuran-1(3H)-one (phenolphthalein cyanate), 3,3-bis(4-cyanato-3-methylphenyl)isobenzofuran-1(3H)-one (o-cresol phthalein cyanate), 9,9'-bis(4-cyanatophenyl)fluorene, 9,9-bis(4-cyanato-3-methylphenyl)fluorene, 9,9-bis(2-cyanato-5-biphenylyl)fluorene, tris(4-cyanatophenyl)methane, 1,1,1-tris(4-cyanatophenyl)ethane, 1,1,3-tris(4-cyanatophenyl)propane, α,α,α'-tris(4-cyanatophenyl)-1-ethyl-4-isopropyl benzene, 1,1,2,2-tetrakis(4-cyanatophenyl)ethane, tetrakis(4-cyanatophenyl)methane, 2,4,6-tris(N-methyl-4-cyanatoanilino)-1,3, 5-triazine, 2,4-bis(N-methyl-4-cyanatoanilino)-6-(N-methylanilino)-1,3,5-triazine, bis(N-4-cyanato-2-methylphenyl)-4,4'-oxydiphthalimide, bis(N-3-cyanato-4-methylphenyl)-4,4'-oxydiphthalimide, bis(N-4-cyanatophenyl)-4,4'-oxydiphthalimide, bis(N-4-cyanato-2-methylphenyl)-4,4'-(hexafluoroisopropylidene)diphthalimide, tris(3,5-dimethyl-4-cyanatobenzyl)isocyanurate, 2-phenyl-3,3-bis(4-cyanatophenyl)phthalimidine, 2-(4-methylphenyl)-3,3-bis(4-cyanatophenyl)phthalimidine, 2-phenyl-3,3-bis(4-cyanato-3-methylphenyl)phthalimidine, 1-methyl-3,3-bis(4-cyanatophenyl)indolin-2-one, and 2-phenyl-3,3-bis(4-cyanatophenyl)indolin-2-one. Other specific examples of the cyanato-substituted aromatic compound represented by formula (7) above also include those obtained by cyanating, by the same method as described above, phenol resins such as a phenol novolac resin and a cresol novolac resin (resins obtained by reacting phenol, alkyl-substituted phenol, or halogen-substituted phenol with a formaldehyde compound such as formalin or paraformaldehyde in an acidic solution by a method known in the art); a trisphenol novolac resin (a resin obtained by reacting hydroxybenzaldehyde with phenol in the presence of an acidic catalyst); a fluorene novolac resin (a resin obtained by reacting a fluorenone compound with a 9,9-bis(hydroxyaryl)fluorene in the presence of an acidic catalyst); a furan ring-containing phenol novolak resin (a resin obtained by reacting furfural with phenol in the presence of a basic catalyst); a phenol aralkyl resin, a cresol aralkyl resin, a naphthol aralkyl resin, a binaphthol aralkyl resin, and a biphenyl aralkyl resin (resins obtained by a known method in the art by reacting a bishalogenomethyl compound represented by $Ar_2$—$(CH_2Y)_2$ ($Ar_2$ represents a phenyl group, Y represents a halogen atom, and the same applies below in this paragraph) with a phenol compound in the presence or absence of an acidic catalyst, resins obtained by reacting a bis(alkoxymethyl) compound represented by $Ar_2$—$(CH_2OR)_2$ with a phenol compound in the presence of an acidic catalyst, resins obtained by reacting a bis(hydroxymethyl) compound represented by $Ar_2$—$(CH_2OH)_2$ with a phenol compound in the presence of an acidic catalyst, or resins obtained by polycondensing an aromatic aldehyde compound, an aralkyl compound, and a phenol compound); a phenol-modified xylene formaldehyde resin (a resin obtained by reacting a xylene formaldehyde resin with a phenol compound in the presence of an acidic catalyst by a method known in the art); a modified naphthalene formaldehyde resin (a resin obtained by reacting a naphthalene formaldehyde resin with a hydroxy-substituted aromatic compound in the presence of an acidic catalyst by a method known in the art); a phenol-modified dicyclopentadiene resin; and a phenol resin having a polynaphthylene ether structure (resins obtained by dehydratively condensing a polyvalent hydroxynaphthalene compound having two or more phenolic hydroxy groups in one molecule in the presence of a basic catalyst by a method known in the art). These are not particularly limited. One of these further cyanate ester compounds can be used alone, or two or more can be used in combination.

A compound generally known in the art can be used as the maleimide compound as long as the compound has one or more maleimide groups in one molecule. Examples of the maleimide compound include, but are not particularly limited to, o-phenylene bismaleimide, m-phenylene bismaleimide, p-phenylene bismaleimide, o-phenylene biscitraconimide, m-phenylene biscitraconimide, p-phenylene biscitraconimide, 4,4'-diphenylmethane bismaleimide, bis(3,5-dimethyl-4-maleimidophenyl)methane, bis(3-ethyl-5-methyl-4-maleimidophenyl)methane, bis(3,5-diethyl-4-maleimidophenyl)methane, 2,2'-bis[4-(4-maleimidophenoxy)phenyl]propane, 4-methyl-1,3-phenylene bismaleimide, 1,6'-bismaleimido-(2,2,4-trimethyl)hexane, 4,4-diphenyl ether bismaleimide, 4,4-diphenylsulfone bismaleimide, 1,3-bis(3-maleimidophenoxy)benzene, 1,3-bis(4-maleimidophenoxy)benzene, 4,4'-diphenylmethane biscitraconimide, 2,2'-bis[4-(4-citraconimidophenoxy)phenyl]propane, bis(3,5-dimethyl-4-citraconimidophenyl)methane, bis(3-ethyl-5-methyl-4-citraconimidophenyl)methane, bis(3,5-diethyl-4-citraconimidophenyl)methane, polyphenylmethane-maleimide, and prepolymers of these maleimide compounds, or prepolymers of these maleimide compounds and amine compounds. One of these maleimide compounds can be used alone, or two or more can be used in combination.

The phenol resin is preferably a phenol resin having two or more hydroxy groups in one molecule, and a phenol resin generally known in the art can be used. Examples of the phenol resin include, but are not particularly limited to, bisphenol A-based phenol resins, bisphenol E-based phenol resins, bisphenol F-based phenol resins, bisphenol S-based phenol resins, phenol novolac resins, bisphenol A novolac-based phenol resins, glycidyl ester-based phenol resins, aralkyl novolac-based phenol resins, biphenyl aralkyl-based phenol resins, cresol novolac-based phenol resins, polyfunctional phenol resins, naphthol resins, naphthol novolac resins, polyfunctional naphthol resins, anthracene-based phenol resins, naphthalene skeleton-modified novolac-based phenol resins, phenol aralkyl-based phenol resins, naphthol aralkyl-based phenol resins, dicyclopentadiene-based phenol resins, biphenyl-based phenol resins, alicyclic phenol resins, polyol-based phenol resins, phosphorus-containing phenol resins, polymerizable unsaturated hydrocarbon group-containing phenol resins, and hydroxy group-containing silicone resins. One of these phenol resins can be used alone, or two or more can be used in combination.

A compound generally known in the art can be used as the epoxy resin as long as the compound has two or more epoxy groups in one molecule. Examples of the epoxy resin include bisphenol A-based epoxy resins, bisphenol E-based epoxy resins, bisphenol F-based epoxy resins, bisphenol S-based epoxy resins, bisphenol A novolac-based epoxy resins, biphenyl-based epoxy resins, phenol novolac-based epoxy resins, cresol novolac-based epoxy resins, xylene novolac-based epoxy resins, naphthalene-based epoxy resins, anthracene-based epoxy resins, trifunctional phenol-based epoxy resins, tetrafunctional phenol-based epoxy resins, triglycidyl isocyanurate, glycidyl ester-based epoxy resins, alicyclic epoxy resins, dicyclopentadiene novolac-based epoxy resins, biphenyl novolac-based epoxy resins, phenol aralkyl novolac-based epoxy resins, naphthol aralkyl novolac-based epoxy resins, aralkyl novolac-based epoxy resins, biphenyl aralkyl-based epoxy resins, naphthol aralkyl-based epoxy resins, dicyclopentadiene-based epoxy resins, polyol-based epoxy resins, alicyclic epoxy resins, or halides thereof. One of these epoxy resins can be used alone, or two or more can be used in combination.

An oxetane resin generally known in the art can be used as the oxetane resin. Examples of the oxetane resin include oxetane; alkyloxetanes such as 2-methyloxetane, 2,2-dimethyloxetane, 3-methyloxetane, and 3,3-dimethyloxetane; and 3-methyl-3-methoxymethyloxetane, 3,3'-di(trifluoromethyl)perfluoxetane, 2-chloromethyloxetane, and 3,3-bis(chloromethyl)oxetane. Examples of commercially available products include OXT-101 (trade name, manufactured by Toagosei Co., Ltd.) and OXT-121 (trade name, manufactured by Toagosei Co., Ltd.). One of these oxetane resins can be used alone, or two or more can be used in combination.

The benzoxazine compound is preferably a compound having two or more dihydrobenzoxazine rings in one molecule, and a compound generally known in the art can be used. Examples of the benzoxazine compound include bisphenol A-based benzoxazine BA-BXZ (trade name, manufactured by Konishi Chemical Ind. Co., Ltd.), bisphenol F-based benzoxazine BF-BXZ (trade name, manufactured by Konishi Chemical Ind. Co., Ltd.), bisphenol S-based benzoxazine BS-BXZ (trade name, manufactured by Konishi Chemical Ind. Co., Ltd.), and phenolphthalein-based benzoxazine. One of these benzoxazine compounds can be used alone, or two or more can be used in combination.

A compound generally known in the art can be used as the compound having a polymerizable unsaturated group. Examples of the compound having a polymerizable unsaturated group include vinyl compounds such as ethylene, propylene, styrene, divinylbenzene, and divinylbiphenyl; monohydric or polyhydric alcohol (meth)acrylates such as methyl (meth)acrylate, 2-hydroxyethyl (meth)acrylate, 2-hydroxypropyl (meth)acrylate, polypropylene glycol di(meth)acrylate, trimethylolpropane di(meth)acrylate, trimethylolpropane tri(meth)acrylate, pentaerythritol tetra(meth)acrylate, and dipentaerythritol hexa(meth)acrylate; epoxy (meth)acrylates such as bisphenol A-based epoxy (meth)acrylate and bisphenol F-based epoxy (meth)acrylate; and benzocyclobutene resins. One of these compounds having a polymerizable unsaturated group can be used alone, or two or more can be used in combination. It is noted that the "(meth)acrylate" conceptually encompasses acrylate and methacrylate corresponding thereto.

The curable resin composition in the present embodiment can further contain, in addition to the compounds and resins described above, a compound acting as a polymerization catalyst for a cyanate ester compound, a maleimide compound, a phenol resin, an epoxy resin, an oxetane resin, and a compound having a polymerizable unsaturated group. Examples of the polymerization catalyst include metal salts such as zinc octanoate, zinc naphthenate, cobalt naphthenate, copper naphthenate, and acetylacetone iron; phenol compounds such as octylphenol and nonylphenol; alcohols such as 1-butanol and 2-ethylhexanol; imidazole derivatives such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethylimidazole, and 2-phenyl-4-methyl-5-hydroxymethylimidazole; amine compounds such as dicyandiamide, benzyldimethylamine, and 4-methyl-N,N-dimethylbenzylamine; and phosphorus compounds such as phosphine compounds and phosphonium compounds. Epoxy-imidazole adduct compounds; peroxides such as benzoyl peroxide, p-chlorobenzoyl peroxide, di-t-butyl peroxide, diisopropyl peroxycarbonate, and di-2-ethylhexyl peroxycarbonate; and azo compounds such as azobisisobutyronitrile can be used as polymerization catalysts. These polymerization catalysts which are commercially available products can be used. Examples of the commercially available products include Amicure PN-23 (trade name, manufactured by Ajinomoto Fine-Techno Co., Inc.), Novacure HX-3721 (trade name, manufactured by Asahi Kasei Corporation.), and Fujicure FX-1000 (trade name, manufactured by Fuji Kasei Kogyo Co., Ltd.). One of these polymerization catalysts can be used alone, or two or more can be used in combination.

The curable resin composition in the present embodiment can contain an inorganic filler. Examples of the inorganic filler include talc, baked clay, unbaked clay, mica, E glass, A glass, NE glass, C glass, L glass, D glass, S glass, M glass G20, short glass fiber (including fine glass powders such as E glass, T glass, D glass, S glass, and Q glass), hollow glass, and spherical glass; silicates such as silica and molten silica; oxides such as titanium oxide, alumina, gibbsite, boehmite, zinc oxide, magnesium oxide, zirconium oxide, and molybdenum oxide; carbonates such as calcium carbonate, magnesium carbonate, and hydrotalcite; hydroxides such as aluminum hydroxide, magnesium hydroxide, and calcium hydroxide; sulfates or sulfites such as barium sulfate, calcium sulfate, and calcium sulfite; borates such as zinc borate, barium metaborate, aluminum borate, calcium borate, and sodium borate; nitrides such as aluminum nitride, boron nitride, silicon nitride, and carbon nitride; carbides such as silicon carbide; titanates such as strontium titanate and barium titanate; and zinc molybdate, silicone composite powders, and silicone resin powders. One of these inorganic fillers can be used alone, or two or more can be used in combination. These fillers differing from each other in shape (spherical or crushed) or size can be mixed and used at an increased content.

The surface of the inorganic filler may be treated in advance with a treating agent for surface treatment. One or more compounds selected from the group consisting of functional group-containing silanes, cyclic oligosiloxanes, organohalosilanes, and alkylsilazanes can be suitably used as a treating agent. Among these treating agents, treating the surface of an inorganic filler (in particular, spherical silica) using organohalosilanes and alkylsilazanes is suitable for hydrophobizing the inorganic filler surface and is preferred from the viewpoint of the excellent dispersibility of the inorganic filler in the curable resin composition.

In addition, the curable resin composition of the present embodiment may optionally contain additives known in the art such as thermoplastic resins, curing catalysts, curing accelerators, coloring pigments, antifoaming agents, surface adjusters, frame retardants, ultraviolet absorbers, antioxidants, photopolymerization initiators, fluorescent whitening agents, photosensitizers, dyes, pigments, thickeners, lubricants, flow modifiers, dispersants, leveling agents, brightening agents, and polymerization inhibitors. Furthermore, the curable resin composition of the present embodiment may optionally contain a solvent. One of these optional additives can be used alone, or two or more can be used in combination.

A solvent generally known in the art can be used as the solvent. Examples of the solvent include ketone solvents such as acetone, methyl ethyl ketone, methyl isobutyl ketone, and cyclohexanone; cellosolve solvents such as propylene glycol monomethyl ether and propylene glycol monomethyl ether acetate; ester solvents such as methyl lactate, methyl acetate, ethyl acetate, butyl acetate, isoamyl acetate, ethyl lactate, methyl methoxypropionate, and methyl hydroxyisobutyrate; alcohol solvents such as methanol, ethanol, isopropanol, and 1-ethoxy-2-propanol; and aromatic hydrocarbons such as toluene, xylene, and anisole. One of these solvents can be used alone, or two or more can be used in combination.

The curable resin composition in the present embodiment can be obtained by mixing the cyanate ester compound described above and optionally a further cyanate ester compound, a maleimide compound, a phenol resin, an epoxy resin, an oxetane resin, a benzoxazine compound, and/or a compound having a polymerizable unsaturated group and various additives, together with a solvent, using a mixer known in the art such as a high-speed mixer, a Nauta mixer, a ribbon blender, a kneader, an intensive mixer, a universal mixer, a dissolver, a static mixer, or the like. For the mixing, methods for adding the cyanate ester compound, various additives, and a solvent are not particularly limited.

The curable resin composition according to the present embodiment can be hardened by heat, light, or the like to obtain a hardened product. The hardened product can be obtained, for example, by melting the curable resin composition or dissolving the curable resin composition in a solvent, and then injecting the resultant into a mold, followed by curing under usual conditions. For heat curing, the curing temperature is preferably in the range of 120° C. to 300° C. from the viewpoint of further accelerating the curing and further suppressing the degradation of the hardened product.

<Purpose of Curable Resin Composition>

The sealing material of the present embodiment contains the curable resin composition and can be produced using the curable resin composition. The method for producing the sealing material is not particularly limited, and a method generally known in the art can be appropriately adopted. For example, the curable resin composition can be mixed with various additives and/or solvents, etc. known to be used for the production of sealing materials, using a mixer known in the art to produce the sealing material. Noted that, for the mixing, the method for adding the curable resin composition, various additives, and solvents is not particularly limited, and a method generally known in the art can be appropriately adopted.

The prepreg for a structural material of the present embodiment contains a base material and the curable resin composition with which the base material is impregnated or coated. The prepreg for a structural material can be produced by impregnating or coating an inorganic and/or organic fiber base material with the curable resin composition, followed by drying, if necessary.

Examples of the base material include, but are not particularly limited to, inorganic fiber base materials such as glass fiber base materials such as glass woven fabrics and glass nonwoven fabrics; organic fiber base materials such as synthetic fiber base materials consisting of woven fabrics or nonwoven fabrics composed mainly of polyamide resin fibers such as polyamide resin fiber, aromatic polyamide resin fiber, and wholly aromatic polyamide resin fiber, polyester resin fibers such as polyester resin fiber, aromatic polyester resin fiber, and wholly aromatic polyester resin fiber, polyimide resin fibers, and fluorine resin fibers, and paper base materials composed mainly of kraft paper, cotton linter paper, or mixture paper of linter and kraft pulp. These known in the art can be appropriately selected, for use, according to the performance required for the prepreg, such as strength, the rate of water absorption, and the coefficient of thermal expansion. Examples of glass constituting the glass fiber base material include, but are not particularly limited to, E glass, C glass, A glass, S glass, D glass, NE glass, T glass, and H glass.

The method for producing the prepreg for a structural material is not particularly limited, and a method generally known in the art can be appropriately adopted. For example, resin varnish is prepared using the curable resin composition described above, and the prepreg can be produced by adopting a method of dipping the base material in the resin varnish; a method of coating the base material with the resin varnish using various coaters; a method of spraying the resin varnish to the base material using a spray; or the like. Among these methods, the method of dipping the base material in the resin varnish is preferred. The impregnating properties of the resin composition for the base material can thereby be improved. In the case of dipping the base material in the resin varnish, a usual impregnation or coating facility can be used. For example, a method for producing a prepreg through conversion to B-stage by impregnating the inorganic and/or organic fiber base material with the resin composition varnish, followed by drying can be adopted.

The fiber-reinforced composite material of the present embodiment contains the curable resin composition of the present embodiment and can be produced using the curable resin composition and reinforcing fiber. As the reinforcing fiber contained in the fiber-reinforced composite material, for example, fiber such as carbon fiber, glass fiber, aramide fiber, boron fiber, PBO fiber, high-strength polyethylene fiber, alumina fiber, and silicon carbide fiber can be used. The form or sequence of the reinforcing fiber is not particularly limited and can be appropriately selected from, for example, woven fabrics, unwoven fabrics, mats, knits, braided cords, unidirectional strands, rovings, and chopped strands. Alternatively, a preform (laminated woven ground fabrics made of the reinforcing fiber, or an integrally sutured product thereof using stitching yarn, or a fiber structure such as a three-dimensional woven fabric or a knitted or braided fabric) may be adopted as a form of the reinforcing fiber. Specific examples of methods for producing these fiber-reinforced composite materials include liquid composite molding methods, resin film infusion methods, filament winding methods, hand lay-up methods, and pultrusion methods. Among these methods, a resin transfer molding method, which is one of the liquid composite molding methods, is adaptable to various purposes because materials other than preforms, such as a metal plate, a foam core, and a honeycomb core can be loaded in molds in advance. Therefore, the resin transfer molding method is preferably used in the large-scale production of composite materials having a relatively complicated shape in a short time.

The adhesive of the present embodiment contains the curable resin composition of the present embodiment and can be produced using the curable resin composition. The method for producing the adhesive is not particularly limited, and a method generally known in the art can be appropriately adopted. For example, the curable resin composition can be mixed with various additives and/or solvents, etc. known to be used for the production of adhesives, using a mixer known in the art to produce the adhesive. For the mixing, the method for adding the curable resin composition, various additives, and solvents is not particularly limited, and a method generally known in the art can be appropriately adopted.

The cyanate ester compound of the present embodiment has excellent solvent solubility and excellent handleability. Containing the cyanate ester compound, the curable resin composition of the present embodiment can achieve a hardened product or the like having a low coefficient of thermal expansion and excellent flame retardancy and heat resistance. Furthermore, the curable resin composition according to the present embodiment has excellent low thermal expansibility, flame retardancy, and heat resistance and is therefore very useful as a highly functional polymer material. The curable resin composition is preferably used as a material excellent thermally, electrically, and in mechanical properties in electrical insulating materials, sealing materials, adhesives, laminating materials, resists, and buildup laminate materials as well as fixation materials, structural members, reinforcing agents, templating materials, etc. in fields such as civil engineering and construction, electrical and electronics, automobiles, railroads, shipping, aircrafts, sport goods, and arts and crafts. Among others, the curable resin composition of the present embodiments is suitable for electrical insulating materials, semiconductor sealing materials, adhesives for electronic components, aircraft structural members, satellite structural members, and railroad vehicle structural members, which are required to have low thermal expansivity, flame retardancy, and a high level of mechanical strength.

EXAMPLES

Hereinafter, the present invention will be described more specifically with reference to Examples. However, the present invention is not intended to be particularly limited by Examples below.

(Measurement of Hydroxy Group (Hereinafter Referred to as an "OH Group") (g/Eq.) Equivalent of Hydroxy Group-Containing Aromatic Compound)

According to JIS-K0070, the OH group equivalent (g/eq.) of a hydroxy group-containing aromatic compound was determined by the pyridine-acetyl chloride method.

(Measurement of Weight-Average Molecular Weight Mw of Cyanate Ester Compound)

10 μL of a solution containing 1 g of the cyanate ester compound dissolved in 100 g of tetrahydrofuran (solvent) was injected to high-performance liquid chromatography (high-performance liquid chromatograph, trade name. "Lachrom Elite" manufactured by Hitachi High-Technologies Corporation.), and analysis was carried out. Two trade-name "TSKgel $GMH_{HR}$-M" (30 cm long×7.8 mm in inside diameter) columns manufactured by Tosho Corp were used, and tetrahydrofuran was used as a mobile phase. The flow rate of a sample in the columns was set at 1 mL/min, and an RI (differential refraction) detector was used as a detector. The weight-average molecular weight Mw was determined by GPC with polystyrene as a standard.

Example 1

Synthesis of Cyanate Ester Compound 1 of Naphthol-Dihydroxynaphthalene Aralkyl Resin (Hereinafter, Abbreviated to "MF27S-3-CN")

MF27S-3-CN represented by the following formula (1) and/or the following formula (2) was synthesized as mentioned later:

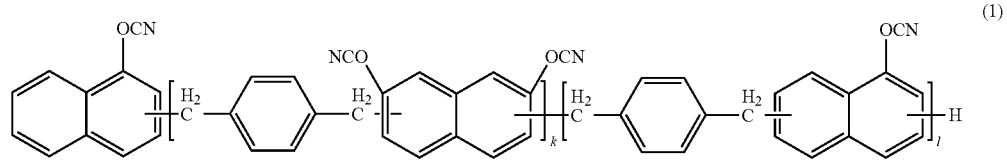

(1)

wherein k represents an integer of 1 to 20, and l represents an integer of 0 to 20; the compound may be a mixture of compounds differing from each other in k and l; and arrangement of repeating units is arbitrary; and

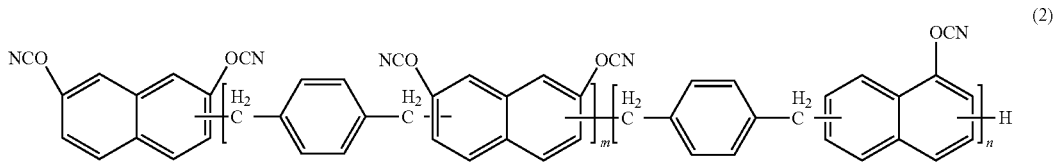

(2)

wherein m and n represent an integer of 0 to 20, and at least one is 1 or larger; the compound may be a mixture of compounds differing from each other in m and n; and arrangement of repeating units is arbitrary.

Synthesis of Naphthol-Dihydroxynaphthalene Aralkyl Resin 1 (Hereinafter, Abbreviated to "MF27S-3-OH")

First, MF27S-3-OH represented by the following formula (3) and/or the following formula (4) was synthesized:

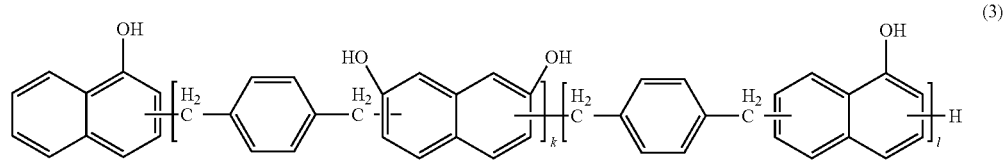

(3)

wherein k represents an integer of 1 to 20, and l represents an integer of 0 to 20; the compound may be a mixture of compounds differing from each other in k and l; and arrangement of repeating units is arbitrary; and

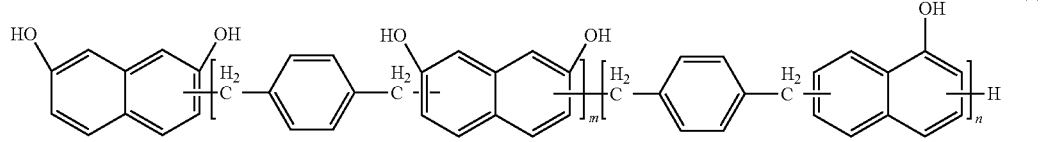

(4)

wherein m and n represent an integer of 0 to 20, and at least one is 1 or larger; the compound may be a mixture of compounds differing from each other in m and n; and arrangement of repeating units is arbitrary.

Specifically, 372.0 g (2.58 mol) of 1-naphthol and 177.4 g (1.11 mol) of 2,7-dihydroxynaphthalene were introduced into a reactor and stirred at 150° C. to be dissolved. Subsequently, 0.17 g of para-toluenesulfonic acid was added to the reactor, and 299.2 g (1.80 mol) of 1,4-bis(methoxymethyl)benzene was added dropwise while raising the temperature to 170° C. over 1 hour. Thereafter, in this state, the reaction was carried out at 170° C. for 3 hours while removing methanol and produced water from the reactor. After the completion of the reaction, the reaction mixture was diluted with 1000 g of a mixed solvent (meta-xylene/MIBK=1/1 (volume ratio)), and the catalyst was removed from the reaction mixture by washing with water. Furthermore, the unreacted starting materials and the mixed solvent were removed from the reaction mixture by steam distillation and vacuum distillation to obtain 599 g of MF27S-3-OH. The obtained MF27S-3-OH had an OH group equivalent of 174 g/eq.

Synthesis of MF27S-3-CN

Next, 500 g (OH group equivalent: 174 g/eq., 2.87 mol based on OH groups, weight-average molecular weight Mw: 760 (the GPC chart is shown in FIG. 1)) of MF27S-3-OH obtained by the method described above and 436.2 g (4.31 mol, 1.5 mol based on 1 mol of the OH groups of MF27S-3-OH) of triethylamine were dissolved in 3000 g of dichloromethane to prepare solution 1.

In a reactor, 300.3 g (4.89 mol, 1.7 mol based on 1 mol of the OH groups of MF27S-3-OH) of cyanogen chloride, 700.7 g of dichloromethane, 465.6 g (4.60 mol, 1.6 mol based on 1 mol of the OH groups of MF27S-3-OH) of 36% hydrochloric acid, and 2887 g of water were mixed, and solution 1 was poured into the reactor over 70 minutes with stirring while the temperature of the solution was kept at −2 to −0.5° C. After the completion of the pouring of the solution 1, the reactor was stirred at the same temperature as above for 30 minutes. Then, a solution containing 174.5 g (1.72 mol, 0.6 mol based on 1 mol of the OH groups of MF27S-3-OH) of triethylamine dissolved in 14.6 g of dichloromethane (hereinafter referred to as "solution 2") was poured into the reactor over 25 minutes. After the completion of the pouring of the solution 2, the reactor was stirred at the same temperature as above for 30 minutes to complete the reaction.

Then, the reaction solution in the reactor was left standing to separate an organic phase from an aqueous phase. The obtained organic phase was washed with 2 L of 0.1 N hydrochloric acid and then washed with 2000 g of water six times. The electroconductivity of a waste liquid from the sixth washing with water was 20 μS/cm to confirm that removable ionic compounds were fully removed by the washing with water.

Figure 2:
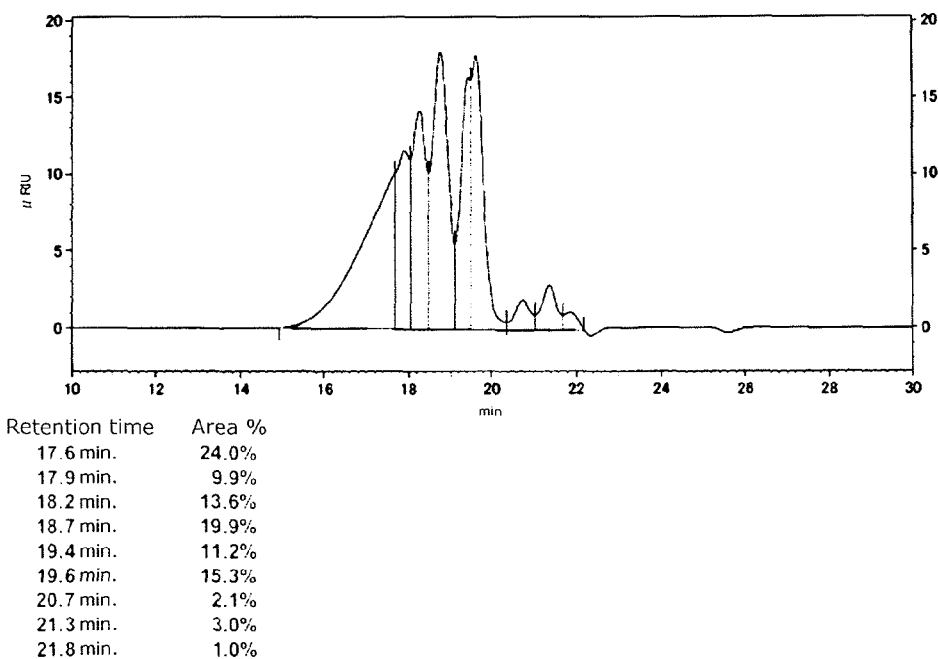
FIG. 2 shows a GPC chart of a cyanate ester compound obtained in an Example.
Figure 3:
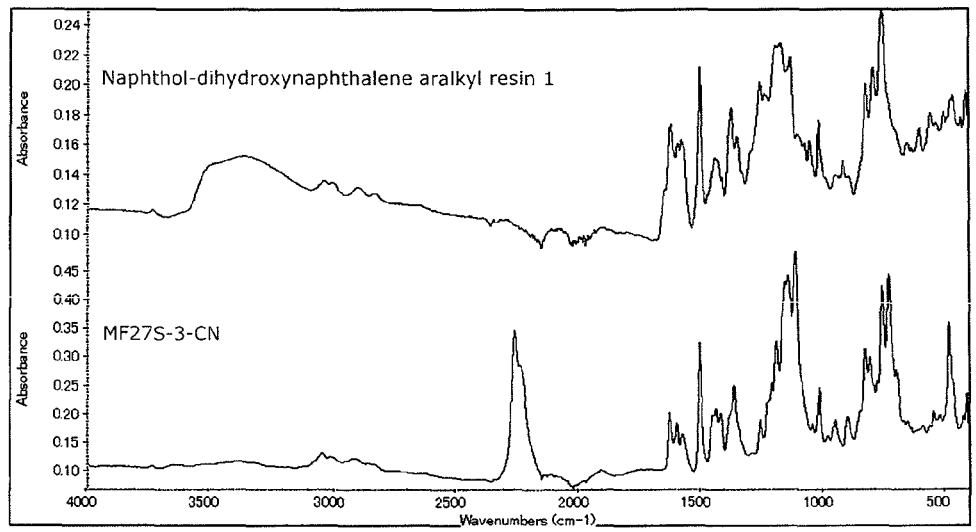
FIG. 3 shows FT-IR charts of a naphthol-dihydroxynaphthalene aralkyl resin and a cyanate ester compound obtained in an Example.

The organic phase thus washed with water was concentrated under reduced pressure and finally concentrated to dryness at 90° C. for 1 hour to obtain 570 g of the cyanate ester compound MF27S-3-CN (dark purple viscous substance) of interest. The obtained MF27S-3-CN had a weight-average molecular weight Mw of 980. The GPC chart thereof is shown in FIG. 2. The IR spectrum of MF27S-3-CN exhibited absorption of a cyanate ester group at 2264 $cm^{-1}$ and did not exhibit the absorption of hydroxy groups. The IR chart thereof is shown in FIG. 3 together with the IR chart of naphthol-dihydroxynaphthalene aralkyl resin 1 (MF27S-3-OH). MF27S-3-CN was able to be dissolved at 50% by mass or more at 25° C. in methyl ethyl ketone.

Example 2

<Preparation of Curable Resin Composition and Preparation of Hardened Product>

100 parts by mass of MF27S-3-CN, which is a cyanate ester compound obtained in Example 1, was introduced into an egg-plant shaped flask, molten by heating at 150° C., and degassed with a vacuum pump. The degassed MF27S-3-CN was injected into the mold described in JIS-K7238-2-2009, accommodated in an oven, and hardened by heating at 180° C. for 3 hours and then at 250° C. for 3 hours to obtain a hardened product of 100 mm in one side and 2 mm in thickness.

Example 3

Synthesis of Cyanate Ester Compound 2 of Naphthol-Dihydroxynaphthalene Aralkyl Resin (Hereinafter, Abbreviated to "MF27S-7-CN")

MF27S-7-CN represented by the following formula (1) and/or the following formula (2) was synthesized as mentioned later:

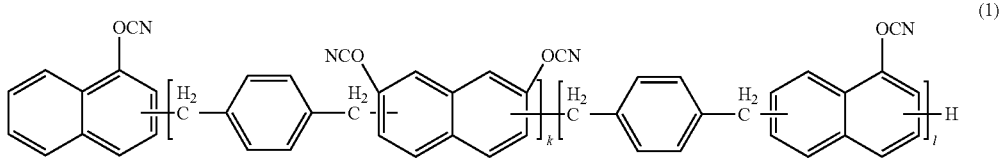

(1)

wherein k represents an integer of 1 to 20, and l represents an integer of 0 to 20; the compound may be a mixture of compounds differing from each other in k and l; and arrangement of repeating units is arbitrary; and

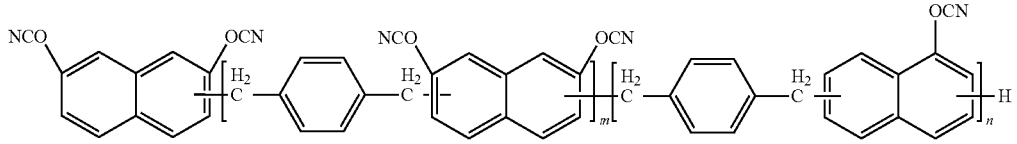

(2)

wherein m and n represent an integer of 0 to 20, and at least one is 1 or larger; the compound may be a mixture of compounds differing from each other in m and n; and arrangement of repeating units is arbitrary.

Synthesis of Naphthol-Dihydroxynaphthalene Aralkyl Resin 2 (Hereinafter, Abbreviated to "MF27S-7-OH")

First, MF27S-7-OH represented by the following formula (3) and/or the following formula (4) was synthesized:

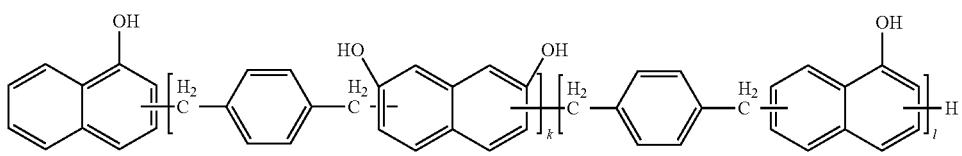

(3)

wherein k represents an integer of 1 to 20, and l represents an integer of 0 to 20; the compound may be a mixture of compounds differing from each other in k and l; and arrangement of repeating units is arbitrary; and

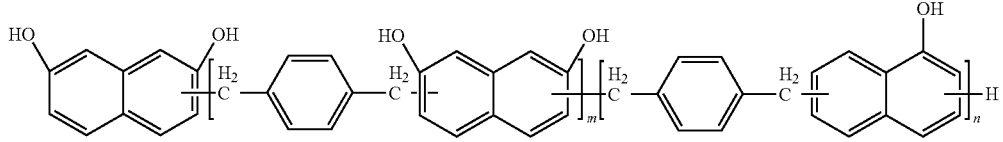

(4)

wherein m and n represent an integer of 0 to 20, and at least one is 1 or larger; the compound may be a mixture of compounds differing from each other in m and n; and arrangement of repeating units is arbitrary.

Specifically, 66.4 g (0.46 mol) of 1-naphthol and 172.4 g (1.08 mol) of 2,7-dihydroxynaphthalene were introduced into a reactor and stirred at 180° C. to be dissolved. Subsequently, 0.073 g of para-toluenesulfonic acid was added to the reactor, and 124.7 g (0.75 mol) of 1,4-bis(methoxymethyl)benzene was added dropwise while raising the temperature to 210° C. over 1 hour. Thereafter, in this state, the reaction was carried out at 210° C. for 3 hours while removing methanol and produced water from the reactor. After the completion of the reaction, the reaction mixture was diluted with 700 g of a mixed solvent (meta-xylene/MIBK=1/1 (volume ratio)), the catalyst and the unreacted starting materials were removed from the reaction mixture by washing with a basic aqueous solution, and the mixed solvent was removed by vacuum distillation to obtain 185 g of MF27S-7-OH. The obtained MF27S-7-OH had an OH group equivalent of 175 g/eq.

Synthesis of MF27S-7-CN

Figure 4:
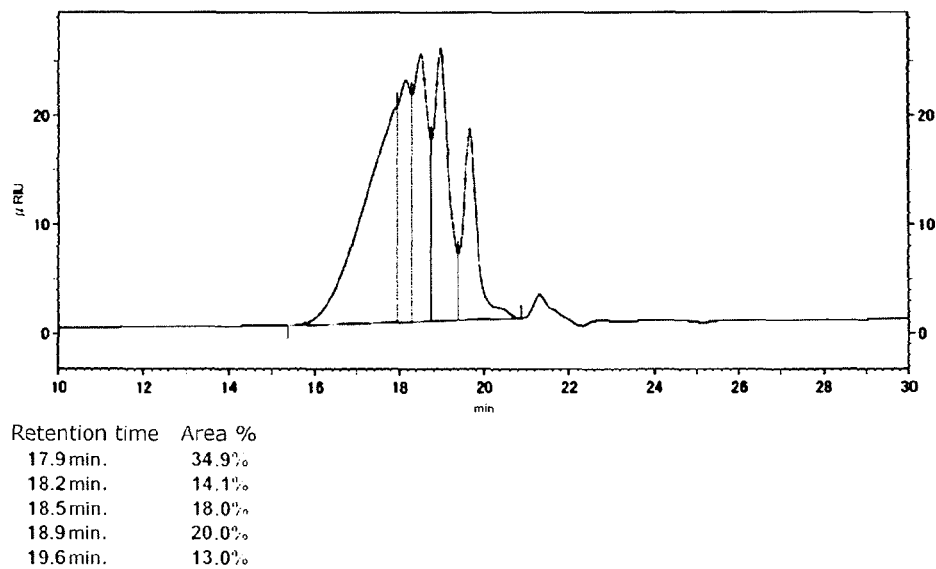
FIG. 4 shows a GPC chart of a naphthol-dihydroxynaphthalene aralkyl resin obtained in another Example.

Next, 15 g (OH group equivalent: 175 g/eq., 0.086 mol based on OH groups, weight-average molecular weight Mw: 960 (the GPC chart is shown in FIG. 4)) of MF27S-7-OH obtained by the method described above and 13.0 g (0.128 mol, 1.5 mol based on 1 mol of the OH groups of MF27S-7-OH) of triethylamine were dissolved in 90 g of dichloromethane and 15 g of tetrahydrofuran to prepare solution 1.

In a reactor, 8.43 g (0.137 mol, 1.6 mol based on 1 mol of the OH groups of MF27S-7-OH) of cyanogen chloride, 19.6 g of dichloromethane, 13.0 g (0.128 mol, 1.5 mol based on 1 mol of the OH groups of MF27S-7-OH) of 36% hydrochloric acid, and 65 g of water were mixed, and solution 1 was poured into the reactor over 20 minutes with stirring while the temperature of the solution was kept at −2 to −0.5° C. After the completion of the pouring of the solution 1, the reactor was stirred at the same temperature as above for 30 minutes. Then, a solution containing 4.0 g (0.039 mol, 0.5 mol based on 1 mol of the OH groups of MF27S-7-OH) of triethylamine dissolved in 4.0 g of dichloromethane (hereinafter referred to as "solution 2") was poured into the reactor over 2 minutes. After the completion of the pouring of the solution 2, the reactor was stirred at the same temperature as above for 30 minutes to complete the reaction.

Then, the reaction solution in the reactor was left standing to separate an organic phase from an aqueous phase. The obtained organic phase was washed with 100 mL of 0.1 N hydrochloric acid and then washed with 100 g of water four times. The electroconductivity of a waste liquid from the fourth washing with water was 20 μS/cm to confirm that removable ionic compounds were fully removed by the washing with water.

Figure 5:
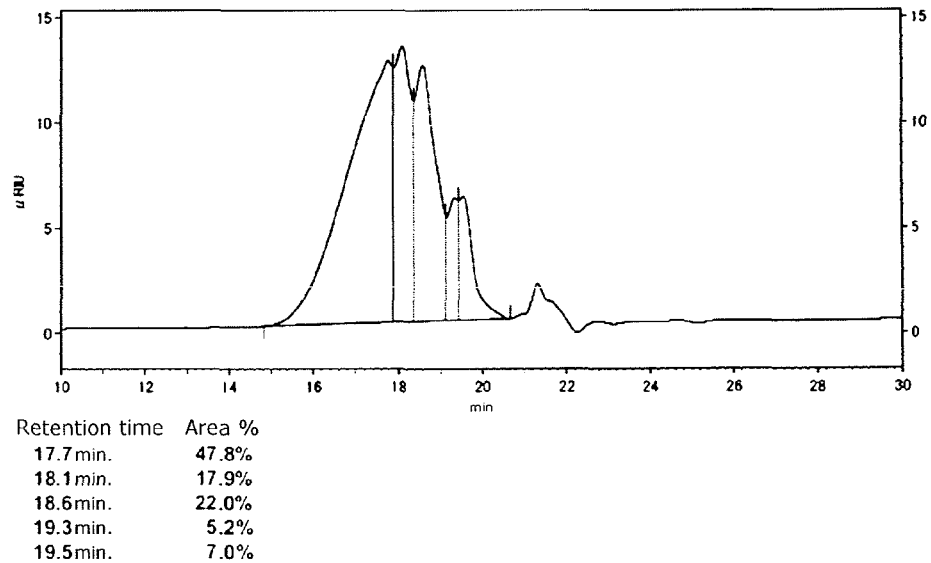
FIG. 5 shows a GPC chart of a cyanate ester compound obtained in another Example.
Figure 6:
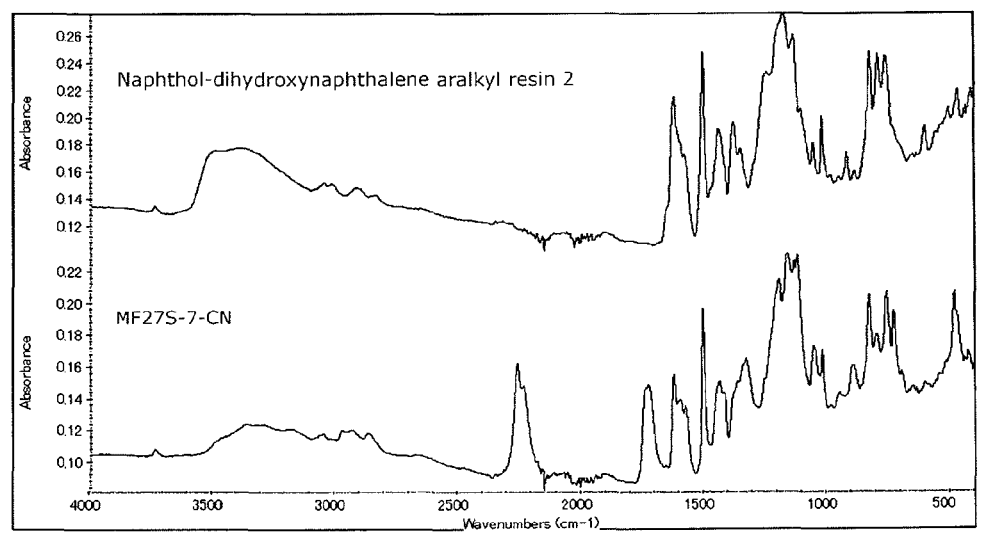
FIG. 6 shows FT-IR charts of a naphthol-dihydroxynaphthalene aralkyl resin and a cyanate ester compound obtained in another Example.

The organic phase thus washed with water was concentrated under reduced pressure and finally concentrated to dryness at 90° C. for 1 hour to obtain 20 g of the cyanate ester compound MF27S-7-CN (dark purple viscous substance) of interest. The obtained MF27S-7-CN had a weight-average molecular weight Mw of 1350. The GPC chart thereof is shown in FIG. 5. The IR spectrum of MF27S-7-CN exhibited absorption of a cyanate ester group at 2239 cm$^{-1}$ and 2265 cm$^{-1}$ and did not exhibit the absorption of hydroxy groups. The IR chart thereof is shown in FIG. 6 together with the IR chart of naphthol-dihydroxynaphthalene aralkyl resin 2 (MF27S-7-OH). MF27S-7-CN was able to be dissolved at 50% by mass or more at 25° C. in methyl ethyl ethyl ketone.

Example 4

A hardened product was obtained in the same way as in Example 2 except that 50 parts by mass of MF27S-7-CN obtained in Example 3 and 50 parts by mass of 2,2-bis(4-cyanatophenyl)propane (trade name "Skylex", manufactured by Mitsubishi Gas Chemical Co., Inc., hereinafter abbreviated to "TA") were used instead of 100 parts by mass of MF27S-3-CN.

Example 5

Synthesis of Cyanate Ester Compound of Dihydroxynaphthalene Aralkyl Resin (Hereinafter, Abbreviated to "MF27S-10-CN")

MF27S-10-CN represented by the following formula (5) was synthesized as mentioned later:

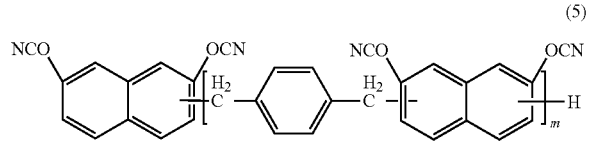

(5)

wherein m represents an integer of 0 to 20; and the compound may be a mixture of compounds differing from each other in m.

Synthesis of Dihydroxynaphthalene Aralkyl Resin (Hereinafter, Abbreviated to "MF27S-10-OH")

First, MF27S-10-OH represented by the following formula (6) was synthesized:

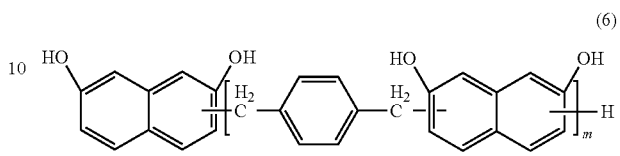

(6)

wherein m represents an integer of 0 to 20; and the compound may be a mixture of compounds differing from each other in m.

Specifically, 160.2 g (1.00 mol) of 2,7-dihydroxynaphthalene was introduced into a reactor and stirred at 210° C. to be dissolved. Subsequently, a mixture composed of 0.049 g of para-toluenesulfonic acid, 10 g of methanol, and 83.1 g (0.50 mol) of 1,4-bis(methoxymethyl)benzene was added dropwise to the reactor over 1 hour. Thereafter, in this state, the reaction was carried out at 210° C. for 2 hours while removing methanol and produced water from the reactor. After the completion of the reaction, the reaction mixture was diluted with 400 g of a mixed solvent (meta-xylene/MIBK=1/1 (volume ratio)), the catalyst and the unreacted starting materials were removed from the reaction mixture by washing with a basic aqueous solution, and the mixed solvent was removed by vacuum distillation to obtain 158 g of MF27S-10-OH. The obtained MF27S-10-OH had an OH group equivalent of 131 g/eq.

Synthesis of MF27S-10-CN

Figure 7:
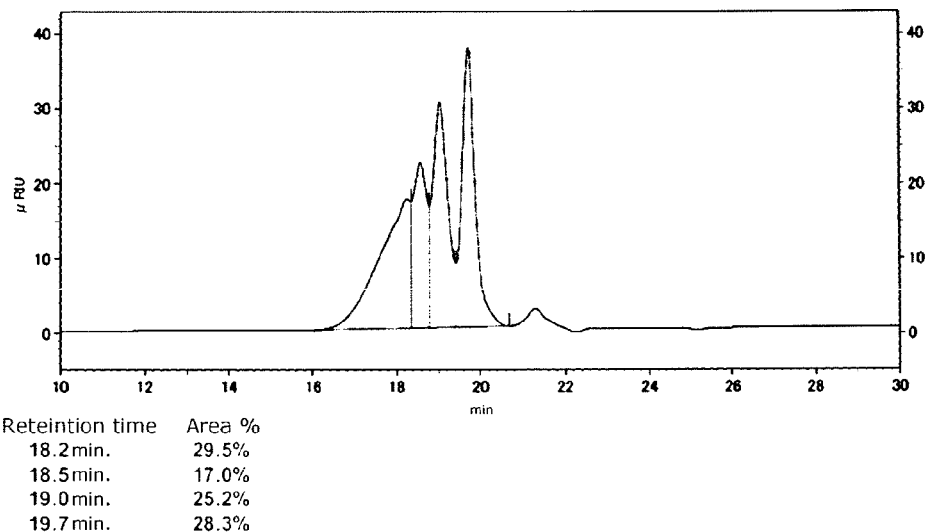
FIG. 7 shows a GPC chart of a dihydroxynaphthalene aralkyl resin obtained in yet another Example.

Next, 20 g (OH group equivalent: 131 g/eq., 0.153 mol based on OH groups, weight-average molecular weight Mw: 650 (the GPC chart is shown in FIG. 7)) of MF27S-10-OH obtained by the method described above and 23.2 g (0.229 mol, 1.5 mol based on 1 mol of the OH groups of MF27S-10-OH) of triethylamine were dissolved in 120 g of dichloromethane and 30 g of tetrahydrofuran to prepare solution 1.

In a reactor, 15.0 g (0.244 mol, 1.6 mol based on 1 mol of the OH groups of MF27S-10-OH) of cyanogen chloride, 35.1 g of dichloromethane, 23.2 g (0.229 mol, 1.5 mol based on 1 mol of the OH groups of MF27S-10-OH) of 36% hydrochloric acid, and 116 g of water were mixed, and solution 1 was poured into the reactor over 30 minutes with stirring while the temperature of the solution was kept at −2 to −0.5° C. After the completion of the pouring of the solution 1, the reactor was stirred at the same temperature as above for 30 minutes. Then, a solution containing 12.4 g (0.039 mol, 0.8 mol based on 1 mol of the OH groups of MF27S-10-OH) of triethylamine dissolved in 12.4 g of dichloromethane (hereinafter referred to as "solution 2") was poured into the reactor over 5 minutes. After the completion of the pouring of the solution 2, the reactor was stirred at the same temperature as above for 30 minutes to complete the reaction.

Then, the reaction solution in the reactor was left standing to separate an organic phase from an aqueous phase. The obtained organic phase was washed with 100 mL of 0.1 N hydrochloric acid and then washed with 100 g of water four times. The electroconductivity of a waste liquid from the fourth washing with water was 20 µS/cm to confirm that removable ionic compounds were fully removed by the washing with water.

Figure 8:
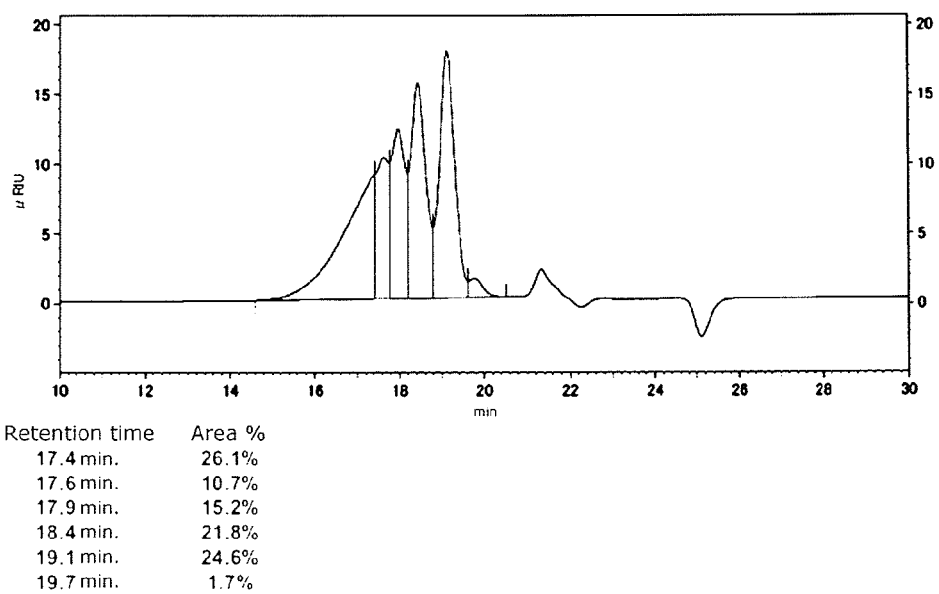
FIG. 8 shows a GPC chart of a cyanate ester compound obtained in yet another Example.
Figure 9:
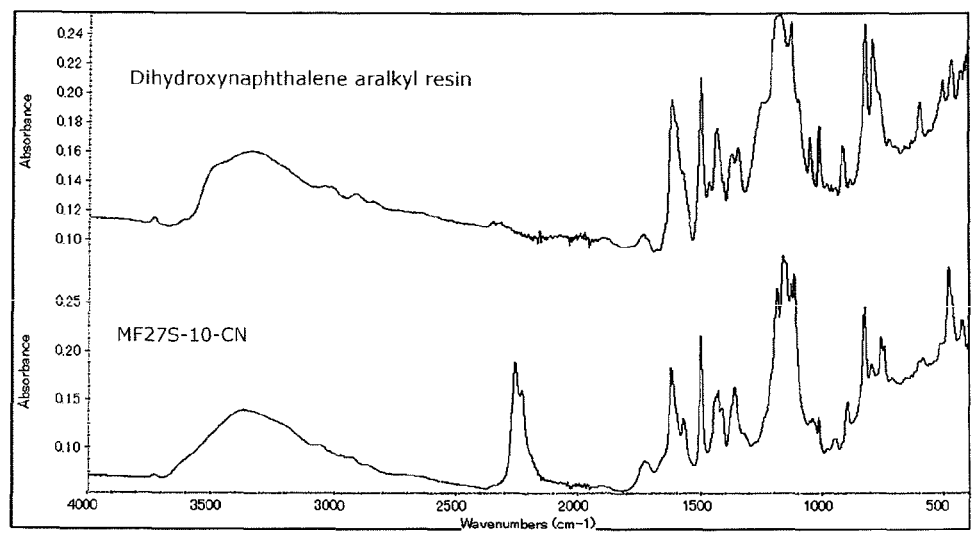
FIG. 9 shows FT-IR charts of a dihydroxynaphthalene aralkyl resin and a cyanate ester compound obtained in yet another Example.

The organic phase thus washed with water was concentrated under reduced pressure and finally concentrated to dryness at 90° C. for 1 hour to obtain 28 g of the cyanate ester compound MF27S-10-CN (dark purple viscous substance) of interest. The obtained MF27S-10-CN had a weight-average molecular weight Mw of 1190. The GPC chart thereof is shown in FIG. 8. The IR spectrum of MF27S-10-CN exhibited absorption of a cyanate ester group at 2237 cm$^{-1}$ and 2266 cm$^{-1}$. The IR chart thereof is shown in FIG. 9 together with the IR chart of dihydroxynaphthalene aralkyl resin (MF27S-10-OH). MF27S-10-CN was able to be dissolved at 50% by mass or more at 25° C. in methyl ethyl ethyl ketone.

Example 6

A hardened product was obtained in the same way as in Example 2 except that 50 parts by mass of MF27S-10-CN obtained in Example 5 and 50 parts by mass of TA were used instead of 100 parts by mass of MF27S-3-CN.

Comparative Example 1

A hardened product was obtained in the same way as in Example 2 except that 100 parts by mass of TA was used instead of 100 parts by mass of MF27S-3-CN. It is noted that TA was able to be dissolved at 50% by mass or more at 25° C. in methyl ethyl ketone.

The properties of each hardened product obtained as described above were evaluated by the methods given below.

[Glass Transition Temperature (Tg)]

According to JIS-K7244-3 (JIS C6481), the dynamic viscoelasticity of the hardened product was measured using a dynamic viscoelasticity measurement apparatus (model "AR2000" manufactured by TA Instruments Japan Inc.) under conditions involving a start temperature of 30° C., an end temperature of 400° C., a temperature increase rate of 3° C./min, and a measurement frequency of 1 Hz. The largest value of a loss elastic modulus (E") obtained in this measurement was used as the glass transition temperature. The glass transition temperature serves as an index for heat resistance.

[Coefficiency of Thermal Expansion]

According to JIS-K-7197-2012 (JIS C6481), a test specimen (size: 5 mm×5 mm×2 mm) of the hardened product was thermomechanically analyzed using a thermomechanical analysis apparatus (trade name "TMA/SS7100" manufactured by SII Nanotechnology Inc.) on the swelling/compression mode under conditions involving a start temperature of 30° C., an end temperature of 330° C., a temperature increase rate of 10° C./min, and a load of 0.05 N (49 mN) to measure the average amount of thermal expansion per ° C. at 60 to 120° C. to determine the coefficiency of thermal expansion.

[Rate of Decrease in Mass (%)]

According to JIS-K7120-1987, the mass of a test specimen (size: 3 mm×3 mm×2 mm) of the hardened product was measured in a nitrogen atmosphere using a thermogravimetry-differential thermal analysis apparatus (trade name "Thermo plus EVO TG8120" manufactured by Rigaku Corp.) under conditions involving a start temperature of 40° C., an end temperature of 500° C., and a temperature increase rate of 10° C./min. The rate of decrease in mass at 500° C. was calculated according to the following expression:

Rate of decrease in mass (%)=$(D-E)/D \times 100$ wherein D represents the mass at the start temperature, and E represents the mass at 500° C. (in the same unit as D). In this context, the "flame retardancy" used herein is defined as a large amount of residues from thermal decomposition, i.e., a low rate of decrease in mass.

[Long-Term Heat Resistance]

The hardened products prepared by the methods described above were stored in a hot-air oven in air at 250° C. for 360 hours, and the glass transition temperatures of the hardened products after storage were measured. Those having a decrease of 20% or less in glass transition temperature after storage were regarded as acceptable, and those exceeded 20% were regarded as unacceptable.

The evaluation results are shown in Table 1.

As is also evident from Table 1, the cyanate ester compound of the naphthol-dihydroxynaphthalene aralkyl resin and the like of the present embodiment were confirmed to have excellent solvent solubility and also have excellent handleability. The hardened product of a curable resin composition containing the cyanate ester compound of the present embodiment was confirmed to have a low coefficiency of thermal expansion and excellent flame retardancy and heat resistance as compared with a hardened product obtained using the conventional cyanate ester compound.

TABLE 1

|  |  |  | Example 1 | Example 2 | Example 3 | Example 4 |
|---|---|---|---|---|---|---|
| Formulation | MF27S-3-CN | Part by mass | 100 | 100 | 0 | 0 |
|  | MF27S-7-CN |  | 0 | 0 | 100 | 50 |
|  | MF27S-10-CN |  | 0 | 0 | 0 | 0 |
|  | TA |  | 0 | 0 | 0 | 50 |
| Physical property of monomer | MEK solubility | % by mass | >50 | — | >50 | — |
| Physical property of hardened product | Tg | ° C. | — | 330 | — | 290 |
|  | Coefficiency of thermal expansion | ppm/° C. | — | 47 | — | 43 |
|  | Rate of decrease in mass | % | — | 20 | — | 38 |
|  | Long-term heat resistance | Judgment | — | Acceptable | — | Acceptable |

TABLE 1-continued

| | | | Example 5 | Example 6 | Comparative Example 1 |
|---|---|---|---|---|---|
| Formulation | MF27S-3-CN | Part by mass | 0 | 0 | 0 |
| | MF27S-7-CN | | 0 | 0 | 0 |
| | MF27S-10-CN | | 100 | 50 | 0 |
| | TA | | 0 | 50 | 100 |
| Physical property of monomer | MEK solubility | % by mass | >50 | — | >50 |
| Physical property of hardened product | Tg | ° C. | — | 320 | 300 |
| | Coefficiency of thermal expansion | ppm/° C. | — | 32 | 59 |
| | Rate of decrease in mass | % | — | 33 | 44 |
| | Long-term heat resistance | Judgment | — | Acceptable | Unacceptable |

The present application is based on a Japanese Patent Application (Japanese Patent Application No. 2015-072689) filed on Mar. 31, 2015, the contents of which are incorporated herein by reference.

INDUSTRIAL APPLICABILITY

The curable resin composition according to the present invention has excellent low thermal expansibility, flame retardancy, and heat resistance and is therefore very useful as a highly functional polymer material. The curable resin composition is preferably used as a material excellent thermally, electrically, and in mechanical properties in electrical insulating materials, sealing materials, adhesives, laminating materials, resists, and buildup laminate materials as well as fixation materials, structural members, reinforcing agents, templating materials, etc. in fields such as civil engineering and construction, electrical and electronics, automobiles, railroads, shipping, aircrafts, sport goods, and arts and crafts, and has industrial applicability to these purposes.

The invention claimed is:

1. A cyanate ester compound having one or more structures selected from the group consisting of structures represented by the following formula (1), formula (2), and formula (5):

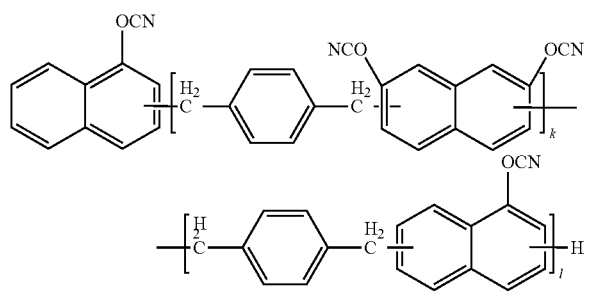
(1)

wherein k represents an integer of 1 or larger, and l represents an integer of 0 or larger; the compound may be a mixture of compounds differing from each other in k and l; and arrangement of repeating units is arbitrary;

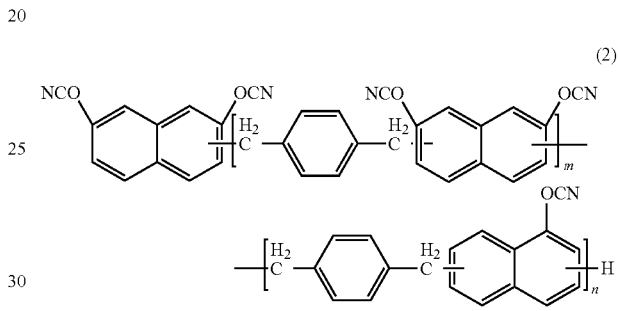
(2)

wherein m and n represent an integer of 0 or larger, and at least one is 1 or larger; the compound may be a mixture of compounds differing from each other in m and n; and arrangement of repeating units is arbitrary; and

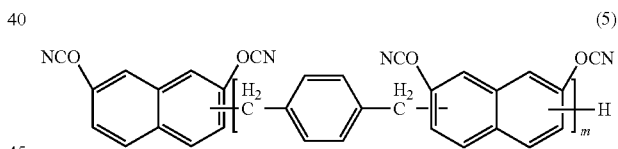
(5)

wherein m represents an integer of 0 or larger; and the compound is a mixture of compounds differing from each other in m.

2. A cyanate ester compound obtained by cyanating one or more resins selected from the group consisting of naphthol-dihydroxynaphthalene aralkyl resins and dihydroxynaphthalene aralkyl resins.

3. The cyanate ester compound according to claim 1 obtained by cyanating one or more resins selected from the group consisting of naphthol-dihydroxynaphthalene aralkyl resins and dihydroxynaphthalene aralkyl resins.

4. The cyanate ester compound according to claim 2, wherein the naphthol-dihydroxynaphthalene aralkyl resin is obtained by reacting 1-naphthol, 2,7-dihydroxynaphthalene, and one or more selected from the group consisting of paraxylene glycol and 1,4-bis(methoxymethyl)benzene in the presence of an acidic catalyst, and the dihydroxynaphthalene aralkyl resin is obtained by reacting 2,7-dihydroxynaphthalene and one or more selected from the group consisting of paraxylene glycol and 1,4-bis(methoxymethyl)benzene in the presence of an acidic catalyst.

5. The cyanate ester compound according to claim 1, wherein the cyanate ester compound has a weight-average molecular weight Mw of 100 to 5000.

6. A curable resin composition comprising a cyanate ester compound according to claim 1.

7. The curable resin composition according to claim 6, further comprising one or more selected from the group consisting of a cyanate ester compound other than the cyanate ester compound, a maleimide compound, a phenol resin, an epoxy resin, an oxetane resin, a benzoxazine compound, and a compound having a polymerizable unsaturated group.

8. A hardened product obtained by curing a curable resin composition according to claim 6.

9. A prepreg for a structural material comprising:
a base material, and
a curable resin composition according to claim 6 with which the base material is impregnated or coated.

10. A sealing material, comprising a curable resin composition according to claim 6.

11. A fiber-reinforced composite material comprising a curable resin composition according to claim 6.

12. An adhesive comprising a curable resin composition according to claim 6.

13. The cyanate ester compound according to claim 3, wherein the naphthol-dihydroxynaphthalene aralkyl resin is obtained by reacting 1-naphthol, 2,7-dihydroxynaphthalene, and one or more selected from the group consisting of paraxylene glycol and 1,4-bis(methoxymethyl)benzene in the presence of an acidic catalyst, and the dihydroxynaphthalene aralkyl resin is obtained by reacting 2,7-dihydroxynaphthalene and one or more selected from the group consisting of paraxylene glycol and 1,4-bis(methoxymethyl)benzene in the presence of an acidic catalyst.

14. The cyanate ester compound according to claim 2, wherein the cyanate ester compound has a weight-average molecular weight Mw of 100 to 5000.

15. The cyanate ester compound according to claim 3, wherein the cyanate ester compound has a weight-average molecular weight Mw of 100 to 5000.

16. The cyanate ester compound according to claim 4, wherein the cyanate ester compound has a weight-average molecular weight Mw of 100 to 5000.

17. A curable resin composition comprising a cyanate ester compound according to claim 2.

18. A curable resin composition comprising a cyanate ester compound according to claim 3.

19. The curable resin composition according to claim 17, further comprising one or more selected from the group consisting of a cyanate ester compound other than the cyanate ester compound, a maleimide compound, a phenol resin, an epoxy resin, an oxetane resin, a benzoxazine compound, and a compound having a polymerizable unsaturated group.

20. The curable resin composition according to claim 18, further comprising one or more selected from the group consisting of a cyanate ester compound other than the cyanate ester compound, a maleimide compound, a phenol resin, an epoxy resin, an oxetane resin, a benzoxazine compound, and a compound having a polymerizable unsaturated group.

* * * * *